United States Patent
Dosch

(10) Patent No.: US 9,689,038 B2
(45) Date of Patent: *Jun. 27, 2017

(54) METHOD FOR REVERSING RECENT-ONSET TYPE 1 DIABETES (T1D) BY ADMINISTERING SUBSTANCE P (SP)

(71) Applicant: Hans-Michael Dosch, Toronto (CA)

(72) Inventor: Hans-Michael Dosch, Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 14/887,435

(22) Filed: Oct. 20, 2015

(65) Prior Publication Data

US 2016/0032394 A1    Feb. 4, 2016

Related U.S. Application Data

(62) Division of application No. 14/244,990, filed on Apr. 4, 2014, now Pat. No. 9,192,647.

(60) Provisional application No. 61/886,804, filed on Oct. 4, 2013.

(51) Int. Cl.
| | |
|---|---|
| *A61K 38/08* | (2006.01) |
| *C12Q 1/68* | (2006.01) |
| *A61P 3/10* | (2006.01) |
| *A61K 9/00* | (2006.01) |
| *A61K 38/04* | (2006.01) |

(52) U.S. Cl.
CPC .......... *C12Q 1/6883* (2013.01); *A61K 9/0019* (2013.01); *A61K 38/046* (2013.01); *A61K 38/08* (2013.01); *C12Q 2600/106* (2013.01); *C12Q 2600/156* (2013.01)

(58) Field of Classification Search
CPC .... A61K 38/08; A61K 38/046; A61K 9/0019; C12Q 1/6883; C12Q 2600/156; C12Q 2600/106
See application file for complete search history.

(56) References Cited

U.S. PATENT DOCUMENTS

| | | | |
|---|---|---|---|
| 2004/0126794 A1* | 7/2004 | Bugawan | C12Q 1/6881 435/6.11 |
| 2009/0221511 A1 | 9/2009 | Dosch et al. | |
| 2009/0312255 A1 | 12/2009 | Dosch et al. | |

FOREIGN PATENT DOCUMENTS

WO    2008/067551 A2    6/2008

OTHER PUBLICATIONS

Andreas Mugge, et al., "Impaired Coronary Dilator Responses to Substance P and Impaired Flow-Dependent Dilator Responses in Heart Transplant Patients with Graft Vasculopathy", JACC, vol. 21, No. 1 pp. 163-170 (1993).

Yan Wang et al., "NeuroPep: a comprehensive resource of neuropeptides", Database, pp. 1-9 (2015).
Office Action received in co-pending U.S. Appl. No. 14/887,427 mailed Jun. 20, 2016.
Abdul-Rasoul, M., Habib, H., and Al-Khouly, M. "'The honeymoon phase' in children with type 1 diabetes mellitus: frequency, duration, and influential factors." Pediatr. Diabetes 7, 101-107 (2006).
Akirav, E., Kushner, J.A., and Herold, K.C. "Beta-cell mass and type 1 diabetes: going, going, gone?" Diabetes 57, 2883-2888 (2008).
Bowden, S.A., Duck, M.M., and Hoffman, R.P. "Young children (<5 yr) and adolescents (>12 yr) with type 1 diabetes mellitus have low rate of partial remission: diabetic ketoacidosis is an important risk factor." Pediatr. Diabetes 9, 197-201 (2008).
Dorfman, R., Tsui, H., Salter, M.W., and Dosch, H.-M. "TRPV1 Genetics." In Vanilloid Receptor TRPV1 in Drug Discovery: Targeting Pain and Other Pathological Disorders, Faltynek, ed. (Hoboken, NJ, USA: John Wiley & Sons, Inc.), pp. 176-229 (2010).
Greenbaum, C.J., Beam, C.A., Boulware, D., Gitelman, S.E., Gottlieb, P.A., Herold, K.C., Lachin, J.M., McGee, P., Palmer, J.P., Pescovitz, M.D., et al. "Fall in C-•—peptide during first 2 years from diagnosis: evidence of at least two distinct phases from composite Type 1 Diabetes TrialNet data." Diabetes 61, 2066-2073 (2012).
Herold, K.C., Hagopian, W., Auger, J.A., Poumian-Ruiz, E., Taylor, L., Donaldson, D., Gitelman, S.E., Harlan, D.M., Xu, D., Zivin, R.A., et al. "Anti-CD3 monoclonal antibody in new-onset type 1 diabetes mellitus." N. Engl. J. Med. 346,1692-1698 (2002).
Koh, Y.H., Tamizhselvi, R., Moochhala, S., Bian, J.S., and Bhatia, M. (2011). "Role of protein kinase C in caerulein induced expression of substance P and neurokinin-1-receptors in murine pancreatic acinar cells." J. Cell. Mol. Med. 15, 2139-2149 (2011).
Lachin, J.M., McGee, P.L., Greenbaum, C.J., Palmer, J., Pescovitz, M.D., Gottlieb, P., and Skyler, J. "Sample size requirements for studies of treatment effects on beta-cell function in newly diagnosed type 1 diabetes." PLoS One 6, e26471 (2011).
Razavi, R., Chan, Y., Afifiyan, F.N., Liu, X.J., Wan, X., Yantha, J., Tsui, H., Tang, L., Tsai, S., Santamaria, P., et al. TRPV1+ sensory neurons control beta cell stress and islet inflammation in autoimmune diabetes. Cell 127, 1123-1135 (2006).
Talchai, C., Xuan, S., Kitamura, T., DePinho, R.A., and Accili, D. (2012). Generation of functional insulin-producing cells in the gut by Foxo1 ablation. Nat. Genet. 44, 406-412, S401 (2012).
Talchai, C. Xuan, S., Lin, H. V., Sussel, L., and Accili, D. Pancreatic beta Cell Dedifferentiation as a Mechanism of Diabetic beta Cell Failure. Cell 150, 1223-1234 (2012).

(Continued)

*Primary Examiner* — Julie Ha
*Assistant Examiner* — Li Ni Komatsu
(74) *Attorney, Agent, or Firm* — Hill & Schumacher

(57) ABSTRACT

Described herein is a treatment comprising the following step: (a) injecting a therapeutically effective amount of a pharmaceutical composition into the celiac artery of an individual, wherein the pharmaceutical composition reverses recent onset Type 1 Diabetes (T1D). Also described is a method for identifying an individual who will be responsive to this treatment. In addition there is described a device containing the pharmaceutical composition for injecting the pharmaceutical composition into the celiac artery.

16 Claims, 5 Drawing Sheets

(56) References Cited

OTHER PUBLICATIONS

Tsui, H., Chan, Y., Tang, L., Winer, S., Cheung, R.K., Paltser, G., Selvanantham, T., Elford, A.R., Ellis, J.R., Becker, D.J., et al. Targeting of pancreatic glia in type 1 diabetes. Diabetes 57, 918-928 (2008).

Tsui, H., Dorfman, R., Salter, M.W., and Dosch, H.-M. The Role of TRPV1 in Diabetes. In Vanilloid Receptor TRPV1 in Drug Discovery: Targeting Pain and Other Pathological Disorders, Faltynek, ed. (Hoboken, NJ, USA: John Wiley & Sons, Inc.), pp. 384-469 (2010).

Tsui, H. Paltser, G., Chan, Y., Dorfman, R., and Dosch, H.M. 'Sensing' the link between type 1 and type 2 diabetes. Diabetes Metab. Res. Rev. 27, 913-918 (2011).

Tsui, H., Razavi, R., Chan, Y., Yantha, J., and Dosch, H.M. 'Sensing' autoimmunity in type 1 diabetes. Trends Mol. Med. 13, 405-413 (2007).

Tsui, H., Winer, S., Chan, Y., Truong, D., Tang, L., Yantha, J., Paltser, G., and Dosch, H.M Islet glia, neurons, and beta cells. Ann. N. Y. Acad. Sci. 1150, 32-42 (2008).

Tsui, H., Winer, S., Jakowsky, G., and Dosch, H.M Neuronal elements in the pathogenesis of type 1 diabetes. Rev. Endocr. Metab. Disord. 4, 301-310 (2003).

Winer, D.A., Winer, S., Shen, L., Wadia, P.P., Yantha, J., Paltser, G., Tsui, H., Wu, P., Davidson, M.G., Alonso, M.N., et al. B cells promote insulin resistance through modulation of T cells and production of pathogenic IgG antibodies. Nat. Med. 17, 610-617 (2011).

Winer, S., Chan, Y., Paltser, G., Truong, D., Tsui, H., Bahrami, J., Dorfman, R., Wang, Y., Zielenski, J., Mastronardi, F., et al. Normalization of obesity-associated insulin resistance through immunotherapy. Nat. Med. 15, 921-929 (2009).

Winer, S., Tsui, H., Lau, A., Song, A., Li, X., Cheung, R.K., Sampson, A., Afifiyan, F., Elford, A., Jackowski, G., et al. Autoimmune islet destruction in spontaneous type 1 diabetes is not beta-cell exclusive. Nat. Med. 9, 198-205 (2003).

Büyükgebiz A, Cemeroglu AP, Böber E, Mohn A, Chiarelli F. Factors influencing remission phase in children with type 1 diabetes mellitus. J. Pediatr. Endocrinol. Metab. 14(9):1585-96 (2001).

Dost A, Herbst A, Kintzel K, Haberland H, Roth CL, Gortner L, Holl RW. Shorter remission period in young versus older children with diabetes mellitus type 1. Exp. Clin. Endocrinol. Diabetes 115(1):33-7 (2007).

Vetter U, Heinze E, Kohne E, Teller WM, Kleihauer E. Relation between the degree of initial metabolic decompensation and the duration of the remission phase in type I diabetes mellitus. Eur. J. Pediatr. 138(1):63-6 (1982).

van Belle TL, Coppieters KT, von Herrath MG. Type 1 diabetes: etiology,immunology, and therapeutic strategies. Physiol. Rev. 91(1):79-118 (2011).

Schober E, Schernthaner G, Frisch H, Fink M. Beta-cell function recovery isnot the only factor responsible for remission in type I diabetics: evaluation of C-peptide secretion in diabetic children after first metabolic recompensation and at partial remission phase. J. Endocrinol. Invest.;7(5):507-12 (1984).

Zmysł owska A, Mł ynarski W, Szadkowska A, Bodalski J. [Prediction of clinical remission using the C-peptide level in type 1 diabetes in children]. Pediatric Endocrinol. Diabetes Metab. 13(2):71-4 (2007).

Agner T, Damm P, Binder C. Remission in IDDM: prospective study of basal C-peptide and insulin dose in 268 consecutive patients. Diabetes Care. 10(2):164-9 (1987).

Böber E, Dündar B, Büyükgebiz A. Partial remission phase and metabolic control in type 1 diabetes mellitus in children and adolescents. J. Pediatr. Endocrinolo-Metab. 14(4):435-41 (2001).

Haneda, E., Higuchi, M., Maeda, J., Inaji, M., Okauchi, T., Ando, K., Obayashi, S., Nagai, Y., Narazaki, M., Ikehira, H., et al. In vivo mapping of substance P receptors in brains of laboratory animals by high-resolution imaging systems. Synapse 61, 205-215 (2007).

Michelgard, A., Appel, L., Pissiota, A., Frans, O., Langstrom, B., Bergstrom, M., and Fredrikson, M. Symptom provocation in specific phobia affects the substance P neurokinin-1 receptor system. Biol. Psychiatry 61, 1002-1006 (2007).

Chan, Y.C., and Leung, P.S. Co-operative effects of angiotensin II and caerulein in NFkappaB activation in pancreatic acinar cells in vitro. Regul. Pept. 166, 128-134 (2011).

Dib, M., Zsengeller, Z., Mitsialis, A., Lu, B., Craig, S., Gerard, C., and Gerard, N.P. A paradoxical protective role for the proinflammatory peptide substance P receptor (NK1R) in acute hyperoxic lung injury. Am. J. Physiol. Lung Cell. Mol. Physiol. 297, L687-697 (2009).

Mansfield, C.S., Watson, P.D., and Jones, B.R. Specificity and sensitivity of serum canine pancreatic elastase-1 concentration in the diagnosis of pancreatitis. J. Vet. Diagn. Invest. 23, 691-697 (2011).

Trivedi, S., Marks, S.L., Kass, P.H., Luff, J.A., Keller, S.M., Johnson, E.G., and Murphy, B. Sensitivity and specificity of canine pancreas-specific lipase (cPL) and other markers for pancreatitis in 70 dogs with and without histopathologic evidence of pancreatitis. J. Vet. Intern. Med. 25, 1241-1247 (2011).

Wan, H., Yuan, Y., Qian, A., Sun, Y., and Qiao, M. Pioglitazone, a PPARgamma ligand, suppresses NFkappaB activation throught inhibition of IkappaB kinase activation in cerulein-treated AR42J cells. Biomed. Pharmacother. 62, 466-472 (2008).

Hasel, C., Bhanot, U.K., Heydrich, R., Strater, J. & Moller, P. Parenchymal regression in chronic pancreatitis spares islets reprogrammed for the expression on NFkappaB and IAPs. Lab. Invest. 85, 1263-1275 (2005).

Notification of Transmittal of the International Search Report and The Written Opinion of the International Searching Authority of the Declaration; International Search Report and Written Opinion of the International Searching Authority received in co-pending PCT Application No. PCT/IB2014/060497, mailed Nov. 18, 2014.

Yi et al, Long-Term Remission of Diabetes in NOD Mice Is Induced by Nondepleting Anti-CD4 and Anti-CDS Antibodies, Diabetes, 2012, 61, pp. 2871-2880.

Examination Report received in Australian Application No. 2014330816 dated May 12, 2016.

\* cited by examiner

METHOD FOR REVERSING RECENT-ONSET TYPE 1 DIABETES (T1D) BY ADMINISTERING SUBSTANCE P (SP)

This application is a divisional of application Ser. No. 14/244,990, filed on Apr. 4, 2014, now U.S. Pat. No. 9,192,647 B2, issued on Nov. 24, 2015. This application also claims benefit of priority to U.S. Provisional Patent Application No. 61/886,804 filed on Oct. 4, 2013, which is incorporated herein by reference in its entirety.

BACKGROUND

Field of the Invention

The present invention relates to neuropeptide therapy of recent-onset Type 1 diabetes (T1D).

Related Art

Current methods of treatment and management of Type 1 Diabetes (T1D) include insulin replacement therapy, pancreas transplantation and islet cell transplantation. Insulin replacement therapy is a challenging and uncomfortable lifelong process plagued by side effects and it does not cure T1D. The clinical challenge is the necessity to adjust insulin release with control of minute-to-minute changing needs. Insulin replacement therapy as practiced saves lives, but cannot prevent chronic succession of hypo- and hyperglycemic events that ultimately degrade micro- and macrovascular functionalities with broadly progressive tissue damage and neuropathy.

SUMMARY

According to one broad aspect, the present invention provides a method comprising following step: (a) injecting a therapeutically effective amount of a pharmaceutical composition into the celiac artery of an individual, wherein the pharmaceutical composition at least partially reverses recent onset Type 1 Diabetes (T1D).

According to a second broad aspect, the present invention provides a device for injecting a pharmaceutical composition into the celiac artery of an individual, wherein the device contains a therapeutically effective amount of the pharmaceutical composition, and wherein the pharmaceutical composition at least partially reverses recent onset Type 1 Diabetes (T1D).

According to a third broad aspect, the present invention provides a method comprising the following step: (a) identifying an individual with recent onset Type 1 Diabetes (T1D) who will respond positively to injecting a therapeutically effective amount of a pharmaceutical composition into the celiac artery of the individual, wherein the pharmaceutical composition at least partially reverses recent onset Type 1 Diabetes (T1D) in the individual.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE PREFERRED EMBODIMENTS

Figure 1:
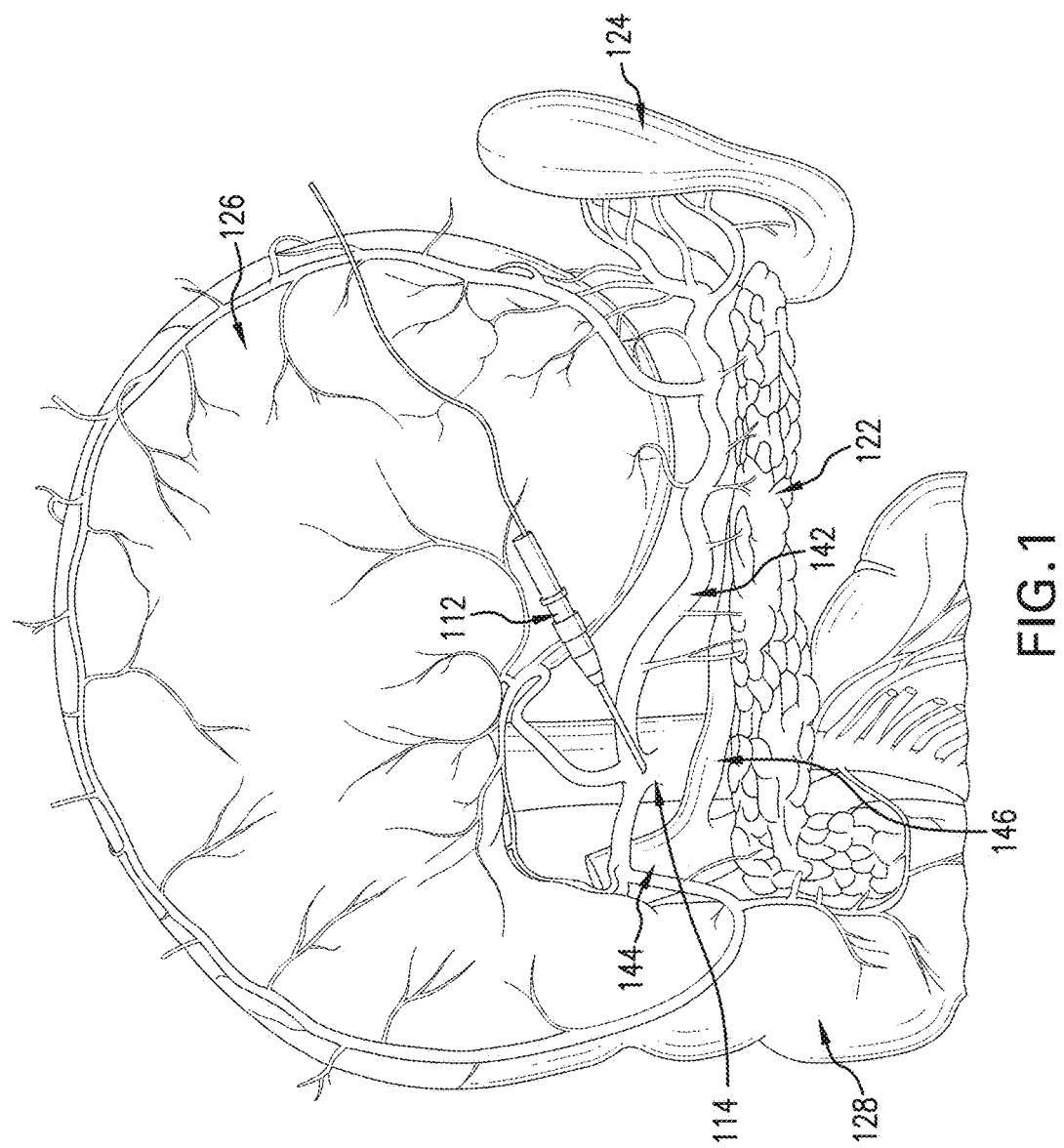
FIG. 1 is a drawing showing a catheter injecting a pharmaceutical composition into the celiac artery of an individual according to one embodiment of the present invention.

Where the definition of terms departs from the commonly used meaning of the term, applicant intends to utilize the definitions provided below, unless specifically indicated.

For purposes of the present invention, a value, a determination or a property is "based" on a particular value, data, information, property, the satisfaction of a condition, or other factor if that value, determination or property is derived by performing a mathematical calculation or logical decision using that value, property or other factor. For example, a determination that an individual has Type 1 Diabetes (T1D) based on the DNA obtained from a saliva sample from the individual For purposes of the present invention, the term "catheter" refers to a thin tube extruded from medical grade materials that facilitates the access of the pancreas.

For purposes of the present invention, the term "individual" refers to a mammal. For example, the term "individual" may refer to a human individual.

For purposes of the present invention, the term "neuropeptide" refers to a small protein-like molecule or peptide released by sensory afferent neurons to communicate with their innervated target tissue.

For purposes of the present invention, the term "recent-onset Type 1 Diabetes (T1D)" refers to a clinical disease onset up to 30 months prior reversal therapy.

For purposes of the present invention, the term "respond positively to injecting a therapeutically effective amount of a pharmaceutical composition into the celiac artery of the individual" refers to an individual for whom this injection of the pharmaceutical composition will at least partially reverse the effect of recent onset Type 1 Diabetes (T1D) in the individual.

For purposes of the present invention, the term "therapeutically effective amount" refers to an amount of substance P administered to an individual that is effective in complete or at least partially reversing recent-onset Type 1 Diabetes in the individual.

For purposes of the present invention, the term "Type 1 Diabetes (T1D)" refers to a form of diabetes mellitus that results from autoimmune destruction or de-differentiation of insulin-producing beta cells of the pancreas.

Description

Transient receptor potential Vanilloid-1, a neuronal $Ca^{++}$-channel, TRPV1, is a major heat-sensing protein in sensory afferent or "pain" nerves. When activated, these nerves release very small biological mediators, neuropeptides, such as the 11-amino acid substance P. sP widens arteries and attracts many elements of the immune system in the area where TRPV1 was activated. It is known that TRPV1 produces a mediated heat sensation. It is known that the burning sensation (generated in the brain) and the local vasodilation/hyperemia (reddening) produced by sP released by activated TRPV1 nerve endings results in the sensing of a heat insult (~45° C.) to the skin: the "ouch" response learned by toddlers encountering something that is "hot".

The sP/sP-receptor (also called NK1R-) pathway is essentially universal, with multiple, general and tissue-specific roles in diverse tissue/organ compartments. In working on the present document, it is estimated from independent searches, that there are more than 30,000 scientific articles that use, measure, map sP and its cousin neuropeptide, CGRP in relation to various in vivo or in vitro interactions and effects. The current <NIH trials.gov >registration site lists nearly 2000 current clinical trials when queried with "substance P".

sP acts as a neurotransmitter, and central neurotransmission along the sP/NK1R pathway was more recently identified as critical modifier in the pathophysiology of varied neuropsychiatric conditions, anxiety, depression, fear, phobia, migraine and diverse stress syndromes, well beyond its early recognized roles in acute and chronic pain, analgesia, emesis—the list of processes involving the sP/sP receptor axis in health and disease is still growing (Haneda et al., 2007[29]; Michelgard et al., 2007[30]).

There is a family of TRPV-like sensors, with TRPV1 the founding and most widely expressed member (Dorfman et al., 2010[4]). TRPV1 integrates multiple and diverse body bitmaps in the brain. When you tickle, break, burn or freeze your toe, the perception is sensed by TRPV1 family-members, signaling to relevant brain centers, which then generate tickle or pain perception to your awareness. The toe will, however, swell because of local release of small "neuropeptides" such as sP. They signal tissue injury and trigger avoidance responses that favor the toe from aggravation and repeat injury/stress.

One group of researchers that has conducted research on diabetes for several decades studied insulin-producing beta cells in the pancreatic islets of Langerhans almost ten years ago. These researchers were puzzled by the observation of dense nervous system elements in- and outside these islets (Winer et al., 2003[20]), which float in a densely packed mass of exocrine pancreas tissue that provides much of the digestive enzymes. Prominent in part of this neuronal network were abundant TRPV1+ sensory nerves whose roles were counterintuitive: what would TRPV1 heat sensors do in the pancreas—a pancreas temperature of 45° C. is not really compatible with life.

In fact, it has been discovered (Razavi et al., 2006[9]), that in mouse models, animals develop diabetes through progressive loss of functional beta cells because their TRPV1 gene has two coding mutations generating a secretory defect, releasing only <5% of neuropeptides, including sP (Razavi et al., 2006[9]; Tsui et al., 2008[12]; Tsui et al., 2007[15]): sP is a growth and survival factor for beta cells, There is a local control circuit, where local insulin ligates insulin receptors in TRPV1 terminals, which activates the channel to release local sP without afferent signaling to the brain. In T1D-prone mice (and also in diabetes patients, see below), beta cells for some time overcome the sP secretory defect, inducing more sP release from "their" TRPV1+ nerve endings with insulin. But too much insulin (called hyperinsulinism) causes hypoglycemia, low blood sugar, and the rest of the body fights that with growing resistance to insulin—a progressively worsening cycle that stresses beta cells already starved for their survival factor, sP. Hyperinsulinism and insulin resistance well before disease onset are typical for the mouse models and also for young patients with high type 1 diabetes risk (Tsui et al., 2011[14]), in fact, it has been found that this is true even for adult patients with Type 2 diabetes risk (Winer et al., 2011[18]; Winer et al., 2009[19]).

Pancreatic delivery of substance P (sP) reverses recent onset Type 1 diabetes mellitus (T1D) within hours in mice (Razavi et al., Cell: 2006[9]). Near synchronous sP receptor binding in pancreatic islets resets the regulatory circuit and globally reverses beta cell stress. This presently proposed, initial, translational study in T1D patients, aims to determine whether an intra-arterial (i.a.) pancreatic sP injection is safe and carries lasting promise for re-differentiation of beta cells and -function, enhanced beta cell mass, reversing hyperinsulinism with normalization of insulin resistance and glucose tolerance as well as down-regulation of local diabetic autoimmunity, as it does in relevant animal models (Tsui et al., Diabetes Metab. Res. Rev: 2011[14]).

Discovered about 80 years ago, substance P has been extensively used in human clinical studies with at best rare adverse events, in part reflecting its extremely short tissue half-life of a minute or less. Decades of experience with human clinical sP trials demonstrate its lack of toxicity. Publications of a selection of more recent clinical sP trials, as well as analytic texts on neuronal elements of T1D, of the remission ("honeymoon") phase of T1D and an overview of research into the role of sP in pancreatitis are found in the Investigator's Brochure, module 1.2.3 of the CTA proposal to Health Canada, Clinical Trials Group.

sP is a non-toxic 11mer neuropeptide with extremely short tissue half-life, released primarily by sensory afferent sensory nerves. <www.trials.gov >still lists nearly 2000 current trials that involve sP, sP-agonists and/or -antagonists, remarkably without sP-attributable adverse events noted there or in the older literature. Although reminiscent in this respect of a lack of toxicity with other neuropeptides in clinical use (e.g. LHRH, TRH, CRH, GHRH, somatostatin), sP's short tissue half-life has so far precluded clinical utility. In the studies proposed here, that short half-life becomes an advantage, permitting strictly local, pancreatic drug delivery with little systemic spillage yet excellent local efficacy (Razavi et al., Cell: 2006[9]; Tsui et al., Diabetes: 2008[12]; Tsui et al., Vanilloid Receptor TRPV1 in Drug Discovery: Targeting Pain and Other Pathological Disorders: 2010[13]; Tsui et al., Diabetes Metab Res Rev: 2011[14]; Tsui et al., Ann. N. Y. Acad. Sci.: 2008[16]).

These animal data demonstrate that a single sP delivery to the diabetic pancreas clears inflammatory lesions rapidly (overnight) and lastingly, through two synergistic mechanisms: 1. immediate relief of beta cell stress with lasting survival support (Razavi et al., Cell: 2006[9]) and (likely) re-activation of de-differentiated or quiescent beta cells (Talchai et al., Nat. Genet.: 2012[10]; Talchai et al., Cell: 2012[11]); 2. rapid, sP-receptor-mediated, selective apoptotic elimination of recently activated, inflammatory lesions in pancreas and local lymphatic tissue. I.a. pancreas injection of sP causes, like in all tissues, brief (minutes), dose-dependent hyperemia. Under experimental conditions, this can be expanded to a transient, pancreatitis-like reaction by preceding injections of caerulein, a potent pancreas toxin (Koh et al., J. Cell. Mol. Med.: 2011[7]). Without such pretreatments, sP pancreas toxicity in rodents has not been observed and it has been found that even large sP doses were not pancreas toxic in a large animal (dog) study. To extend knowledge of potential toxicity to children is a major goal of the present study.

Recently, this has, for essentially the first time, been achieved in animal models, providing a strong rationale and impetus to translate this physiological, therapeutic strategy to patients, without systemic toxicities, based on thousands of previous sP trials.

In one embodiment of the present invention, as shown in FIG. 1, a catheter 112 containing a pharmaceutical composition is used to inject a therapeutically effective amount of the pharmaceutical composition into the celiac artery 114 of an individual to thereby partially reverse recent onset Type 1 Diabetes (T1D). Catheter 112 is attached to a supply (not shown in FIG. 1) of the pharmaceutical composition also shown in FIG. 1 is the pancreas 122, spleen 124, stomach 126, duodenum 128, lienal artery 142, portal vein 144 and lienal vein 146.

In one embodiment of the present invention, the pharmaceutical composition so injected may completely reverse recent onset T1D. In one embodiment of the present invention, the composition may transiently for months to years reverses recent onset T1D. In one embodiment of the present invention, the pharmaceutical composition aids storage, production and release of insulin by beta cells in a pancreas. In one embodiment of the present invention, the pharmaceutical composition comprises a neuropeptide. In one embodiment of the present invention, the pharmaceutical composition comprises substance P. In one embodiment of the present invention, substance P is dissolved in saline in the pharmaceutical composition.

In one embodiment of the present invention, the individual treated as shown in FIG. 1 is diagnosed with Type 1 Diabetes (T1D). In one embodiment of the present invention the individual is a human. In one embodiment, when the individual is a human, therapeutically effective amount of the pharmaceutical composition is at least 10 nmol/kg. In one embodiment, when the individual is a human, therapeutically effective amount of the pharmaceutical composition is at least 50 nmol/kg. In one embodiment, when the individual is a human, therapeutically effective amount of the pharmaceutical composition is at least 100 nmol/kg. In one embodiment, when the individual is a human, therapeutically effective amount of the pharmaceutical composition is at least 250 nmol/kg.

Unexpected neuronal elements in diabetes development have been discovered (Tsui et al., Rev Endocr. Metab. Disord.: 2003; Winer et al., Nat Med: 2003[17]. Subsequently, it has been demonstrated (Razavi et al., Cell: 2006[9]) that a critical element of T1D development is pancreatic sP deficiency, reflective of mutations in the NOD mouse TRPV1 gene. These mutations generate a hypofunctional/hyposecretory phenotype (Tsui et al., Vanilloid Receptor TRPV1 in Drug Discovery: Targeting Pain and Other Pathological Disorders: 2010[13]; Tsui et al., Trends Mol. Med.: 2007[15]).

A single, pancreatic sP injection via the celiac artery reversed recent onset T1D in NOD mice for 4-6 months without any insulin therapy, a period approximately equivalent to about 6-8 years in humans (Tsui et al., Diabetes: 2008[12]).

Human TRPV1 is extremely polymorphic, with thousands of different allele combinations in Caucasian and Asian populations, while it is a monomorphic gene in regions of low T1D incidence, e.g. Africa (Dorfman et al., Vanilloid Receptor TRPV1 in Drug Discovery: Targeting Pain and Other Pathological Disorders: 2010[4]). Sequencing of over 8000 Caucasian T1D patients and controls demonstrates significant bias in TRPV1 allele selection, which share predominantly hypofunctional phenotypes in transfection studies (unpublished interim results, Toronto-Pittsburgh-Helsinki TRPV1 consortium).

It has been directly demonstrated that systemic sP deficiency by a newly developed HNK1R (sP receptor) ligation assay in the majority of T1D patients, finding intermediate levels in a sizable subset of first degree relatives (Cheung, R. K. et al., manuscript in preparation).

The fundamental link between TRPV1, beta cells and autoimmunity previously discovered extends to metabolic syndrome and Type 2 diabetes, emphasizing the fundamental role of neuronal controls in diabetes endocrinology (Tsui et al., Diabetes Metab Res Rev: 2011[14]; Winer et al., Nat Med: 2011[18]; Winer et al., Nat Med: 2009[19]).

A large animal study in dogs has recently been completed, seeking evidence for sP-induced pancreas toxicity following pancreatic injection of sP via the celiac artery. No drug-induced toxicity was found over a study-relevant dose range, using a broad screen of repetitive biochemical blood tests (>1200 assays) as well as extensive histopathology studies conducted blindly at the University of Toronto Center for Phenogenomics by veterinary pathologists NOT associated with the proposed trial. The injections were conducted by the Sick Kids' clinical imaging team. Since this Vanilloid-Genetics-sponsored study is unlikely to be published by itself, excerpt imaging data are provided in the Protocol Addendum, showing the pancreas-selective, rapidly transient (~7 min) sP effect as measured with a co-injected, inert blue dye marker. The short-lived, physiological sP responses (hyperemia→pancreas→selective hyperperfusion and extravasation→normal pancreas appearance) illustrate the core effects expected to be duplicated in T1D patients.

The study has 3 stages (A, B, C), applying a cross-over design where all patients ultimately receive the intervention: Stage A, toxicity and sP dose finding, 12 patients; Stage B, limited efficacy test, 40 randomized patients, cross-over design; Stage C, follow-up to 6 months, all patients, possible extension of follow-up by 6 months.

The primary objective of Stage A is to determine if there are unexpected adverse events with pancreatic delivery of sP in recent (<30 months) onset Type 1 Diabetic patients with basal c-Peptide levels of ≥0.2 pmoles/mL. The second objective of Stage A is to determine whether sP injection at doses of 10, 50, 100 or 250 nmoles/kg BW (3 patients per dose) improve insulin need and/or basal or stimulated c-Peptide levels comparing pre-injection and day 20-22 post-injection mixed meal tolerance (MMTT) data. If one or more Stage A patients initially received an ineffectively small dose, an effective dose may be offered towards the end of the trial.

The primary objective of Stage B is to determine the prevalence of sP-treated patients whose stimulated (MMTT) c-Peptide levels are significantly elevated above base line, 3 weeks post-intervention ("Responders"). The secondary objective of Stage B is to determine if Responders show reduced insulin need, improved hyperinsulinism and improved/normalized glycemia, 3 weeks post-intervention (MMTT data).

The primary objective of Stage C is to determine if Responders sustain treatment effects at 6 months post intervention, or longer, if follow up is extended with a pre-planned DSMB-approved protocol change.

These study objectives acknowledge the realities of an initial translational effort with a stepwise approach to test its potential clinical utility, confirm the absence of unexpected toxicities and generate tentative answers to two core functional questions: does human T1D respond to sP like mouse T1D, and what is the likely longevity of such effects?

The study objectives parallel previously published animal studies as closely as possible (Razavi et al., Cell: 2006[9]; Tsui et al., Vanilloid Receptor TRPV1 in Drug Discovery: Targeting Pain and Other Pathological Disorders: 2010[13]; Tsui et al., Trends Mol. Med.: 2007[15]; Tsui et al., Ann N Y Acad. Sci.: 2008[16]). Clinically, this post-onset study is based on 2012 publications—an NIH-TrialNet meta-study of the first 2 years after T1D onset (Greenbaum et al., Diabetes: 2012[5]) and research reports collectively documenting the unexpectedly slow beta cell death/loss post onset (Talchai et al., Nat. Genet.: 2012[10]; Talchai et al., Cell: 2012[11]).

Figure 2:
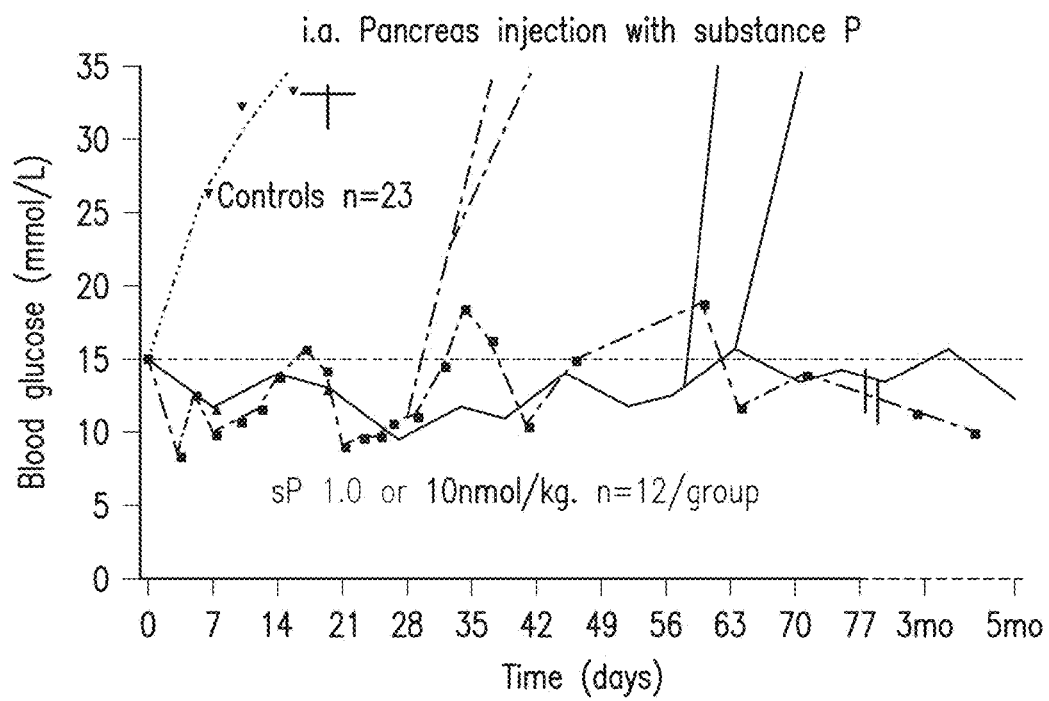
FIG. 2 is a graph showing changes in blood glucose levels, in recent onset diabetic mice, following intra-arterial injection of the pancreas with substance P (sP).

One of the several ways to confirm various conclusions about sP (Tsui, 2010[13]; Tsui et al., 2008[12]) was to inject sP into the pancreas of newly diabetic mice, a rather benign therapy as sP is a physiological, non-toxic molecule that is quite fragile and inactivated in tissue by dedicated and non-specific proteolytic degradation as well as by binding to common NK1R in tissue within seconds. As shown in FIG. 2, sP-injected diabetic mice rapidly responded to the treatment, normalizing blood sugars and other metabolic abnormalities typical for acute diabetes. Control animals injected with vehicle (saline) only rapidly succumbed from diabetes. In some way reminiscent of re-booting a crashed computer, sP injection had lasting effects re-establishing normal insulin control for months, although diabetes would eventually recur—but will again respond to a single sP injection.

Figure 3:
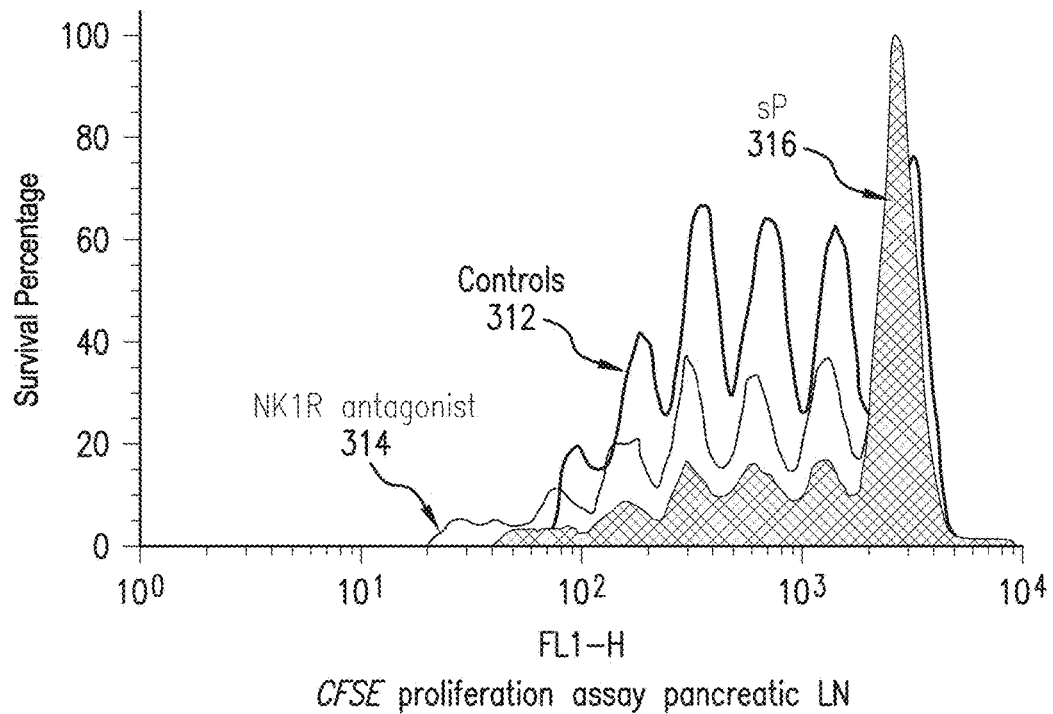
FIG. 3 is a graph illustrating the CFSE T cell proliferation assay inside the pancreatic lymph node of a transgenic, diabetic mouse carrying a diabetogenic T cell receptor (TCR).

In this, the action of sP has several aspects, prominently acting still as beta cell survival factor promoting beta cell regeneration/re-differentiation. The unexpected bonus was, however, that hemopoietic cells, including autoreactive lymphocytes that target islets and beta cells, are for a brief time during activation highly sensitive to sP: binding to sP receptors for a brief period sets a death signal that kills the respective lymphocyte via a form of apoptotic, programmed death response. In fact, the immune system normally employs sP to terminate every-day immune responses: in inflammatory tissue undergoing an immune response, it is necessary not only to initiate but to limit that process. FIG. 3 is a snap shot of what happens in pancreatic lymph nodes, the "breeding place" for autoimmune lymphocytes. The in vivo proliferation of these autoimmune T cells were measured as waves of clonal expansion by cell division, each of the peaks in the figure represents 1 cell division inside the pancreatic lymph node: there were many divisions in the diabetic controls (312), i.e. they rapidly generate many more autoimmune T cells that can kill insulin-secreting beta cells. As shown in FIG. 3, most T cells in sP treated mice (314) did not divide at all (pink shading) in fact they die. While sP-treated mice that also received an sP receptor (NK1R) antagonist (316) showed survival of at least two thirds of the pathogenic T cell clones. Thus, sP injections promote beta cell survival, regeneration and re-differentiation, while, at the same time, selectively eliminating autoimmune cell pools that mediate beta cell death and diabetes (Razavi et al., 2006[9]; Tsui et al., 2008[12]; Tsui et al., 2007[15]).

In previous studies of intra-arterial (pancreas) sP injection into recent-onset diabetic mice (Razavi et al., 2006[9]), pancreas pathology consistent with pancreatitis over a dose range of 0.01-250 nmol/kg has not been observed (the standard dose was 1-10 nmol/kg).

Figure 4:
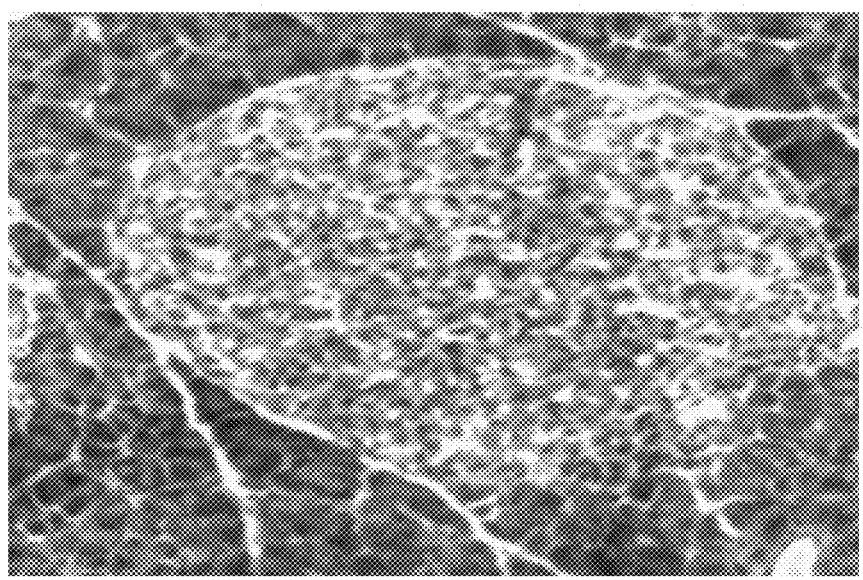
FIG. 4 is an image of a typical, no longer infiltrated islet after recent onset Type 1 diabetes and intra-arterial pancreatic substance P delivery.
Figure 5:
FIG. 5 is an image showing vasodilated pancreatic tissue in mice, following intra-arterial pancreas injection with substance P plus Evans Blue dye marker (observe: pancreas-selective, pancreatic tissue is indicated by arrow 512)).

FIG. 4 shows islets from mice with recent onset Type 1 diabetes. The top shows a clean, no longer inflamed islet of an sP injected mouse (1 nmol/kg). FIG. 5 shows an infiltrated islet from a control, diabetic mouse injected with vehicle (saline). Both islets are surrounded by normal exocrine pancreas tissue without any lesions typical for pancreatitis.

A large animal study of pancreatic sP injection in dogs, using modern pancreatitis diagnostics is currently being conducted (Mansfield et al., 2011[33]) and histopathology for the detection of possible pancreatitis lesions. Data are expected to be complete within about two weeks of this writing, in time for the anticipated Pre-CTA meeting. Dogs are a rational choice of large animal experimental model, since Dogs spontaneously develop pancreatitis, have successfully been used in studies of experimental pancreatitis and well tested diagnostics are available (Trivedi et al., 2011[34]).

The typical, mostly rodent, studies of pancreatitis induction that focus on the role of sP, demonstrated the vasodilation effect of the drug and, in fact, previously published sP injection data documented the same, using the commonly employed Evans Blue dye tracing strategy (Razavi et al., 2006[9]), see FIG. 5. In FIG. 5, pancreatic tissue is indicated by arrow512.

Beyond brief, transient (minutes) tissue hyperperfusion following sP injection, the drug does not cause tissue damage or pancreatitis-like disease. For disease induction, the standard experimental pancreatitis model employs multiple high dose injections of the toxic secretagogue caerulein (Koh et al., 2011[7]).

This protocol duplicates many aspects of spontaneous pancreatitis, including elevation of both, endogenous sP and sP receptor expression in pancreatic acinar cells, the active site of pancreatitis development. In the exocrine pancreas, elevation of sP/sP receptor is part of the NFκB pro-inflammatory transcription pathway and begins to play a role in disease progression 3-4 days after induction with caerulein (Chan and Leung, 2011[31]; Hasel et al., 2005[36]; Wan et al., 2008[35]).

While sP is one of the many elements that characterize the inflammatory pancreatitis lesion, it does not elicit activation of this transcription pathway in acinar cells. While sP has long been a member of the multi-molecular response program caused by tissue injury, binding of sP to its receptor, NK1R, in fact can transmit a potent anti-inflammatory net signal that explains the enhanced severity of some inflammatory responses to tissue damage in NK1R$^{null}$ knock-out mice (Dib et al., 2009[32]).

The injection protocol is described as: Following placing the femoral catheter to the celiac artery under real-time imaging control, the dose finding sP amounts or the Stage B study intervention dose (10, 50, 100 or 250 nmol/kg BW, dissolved in 5 or 10 mL saline (see above), are injected over a 3 minute period. The rationale: Steady rate injection was used in all mouse studies, alternative rate injection timing were compared in the canine study without finding any differences.

In one embodiment of the present invention, the amount of sP administered to a patient may be 10-100 nmol/kg BW, dissolved in 5 or 10 ml saline.

In another embodiment of the present invention, the amount of sP administered to a patient may be 100-250 nmol/kg BW, dissolved in 5 or 10 ml saline.

Figure 6:
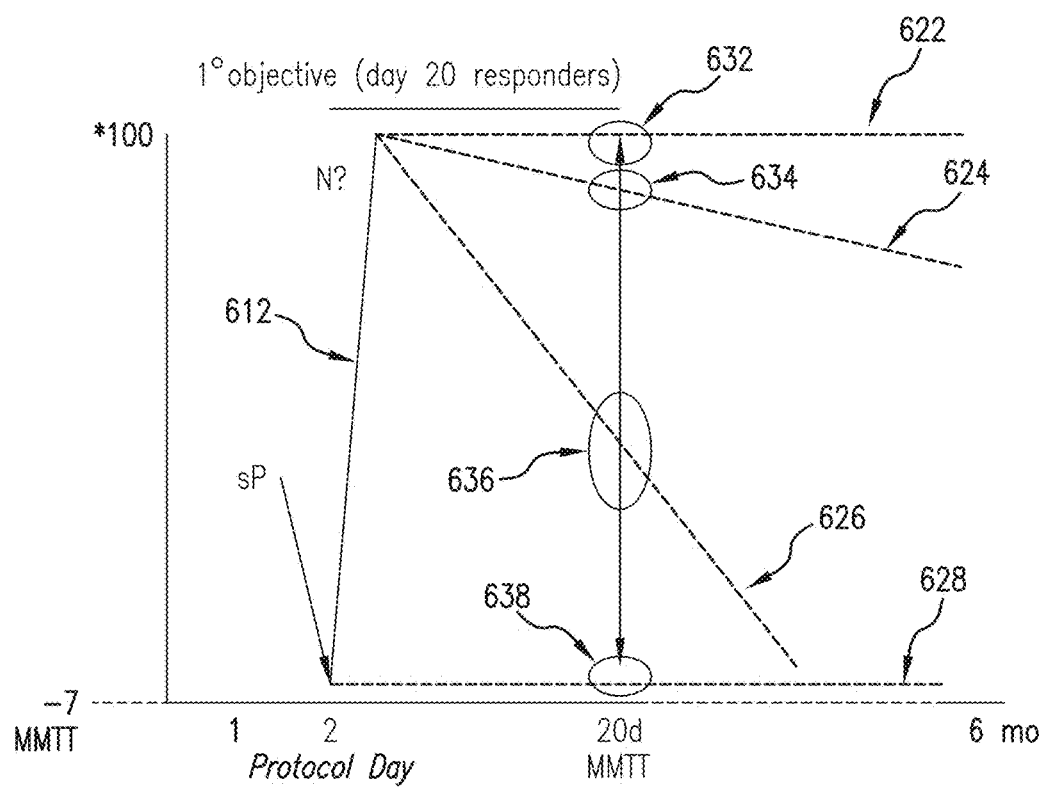
FIG. 6 is a graph that illustrates alternative outcome models of the overall study plan.

As shown in FIG. 6, the overall study plan is based on the assumption that if the intervention has effects comparable to those observed in NOD mice, these should at least to some extent resemble that biology. Thus, the desired effects on T1D endocrinology should: (1) occur rapidly after injection of the short lived sP (612) and (2) c-Peptide (or the other measures (see legend of FIG. 6) should follow one or more possible outcomes shown (622, 624, 626, and 628).

These outcomes are measured by a mixed meal tolerance test, MMTT, on day 20 post-intervention (632, 634, 636, and 638). Responders are defined to follow lines A, B or C, non-responders, line D. All patients are then be entered into the 6 month follow up, Stage C, under standard care—although surveillance and therapy of Responders might have to be modified, as dictated by their T1D status.

This study is described as open-label, randomized, crossover clinical trial. Minimal Duration: 6 month after last patient received intervention; extension of Stage C: Followup to 12 months should be considered if treatment responders are identified.

Stage A is a dose finding and toxicity study. This stage determines if a single sP dose of 10, 50, 100 or 250 nmol/kg BW (1) generates biochemical signs of pancreatitis or other organ dysfunctions in eligible trial patients; or (2) improves endocrine/metabolic T1D parameters. These doses were well tolerated in rodent and canine studies (Module 1.2.3.5). Each of these patients undergoes an MMTT 7- 14d before receiving the intervention. The dose range was selected from animal experience: 50- 250 nmol/kg were equally effective and lasting, 10 less and 1 nmoles marginally so. Four patient groups of three are be injected with clinical trial-grade sP, in each dose group. VanilloidGenetics Inc has designed and outsourced the manufacture and validation of a clinical grade injectable, pediatric (sP-ped) and a regular/adolescent injectable drug formulation (sP-R/A) in a Health Canada-approved, commercial cGMP facility.

Stage A patients are recruited first and randomized when consented to a given sP dose (SASS procedure)—there is not a placebo. Starting with the lowest dose, three patients receive 10 nmoles sP/kg, the next three, 50 nmoles sP/kg, followed by 100 and 250 nmoles sP/kg each, in the last two groups.

Stage B patients are randomized to the 1st or 2nd treatment group. Based on animal data, it is expected that the maximal response to be observed at 50-100 nmoles/kg. Study physicians, together with the IGT angiographic team determines on clinical grounds if patients receive the intervention in 5 or 10 mL saline solution. At least 2 to 3 days of observation between groups is planned, but this period may be modified by study management as the clinical experience grows. Blood chemistries relevant to pancreas and liver and enteric function are monitored after injection. Patients are monitored (see below, standard care) for insulin need and euglycemia.

The rationale behind Stage A is that Stage A generates the first patient data. T1D reversal in recent onset diabetic mice occurs within hours along mechanistic pathways quite well understood. It is expected that sP effects might be rather prompt in patients as well, given the fast kinetics of sP-receptor ligation with its positive survival effects in beta cells and its negative survival effects on the pancreatic autoimmune-infiltrate. The Stage A strategy covers a judicious drug dose range and it proceeds cautiously—although there is no reason to expect any drug toxicities—and it generates the experience needed and the drug dose used for Stage B. The Stage A strategy and cohort size was discussed and incorporated in the final minutes of a pre-CTA meeting with Health Canada (Investigators Brochure, Module 1.2.3.1). In this pre-CTA meeting, it was also discussed that if an effective sP dose emerges in Stage A, it would be ethical to offer Stage A patients that received a lower dose, a second injection at the optimal dose by the end of Stage B may be offered, about 4 weeks after study start and as scheduling allows. This does not jeopardize conclusions derived from this study stage or the study overall, as repeat injections after treatment failure are ultimately part of the follow-up plan, albeit at intervals anticipated in the range of years.

Stage B of the study is the intervention stage. Altogether 40 eligible patients with recent onset T1D receive the Stage A derived sP dose of choice by cannulation of the celiac artery under imaging guidance. The rationale: T1D reversal is an essentially binary (yes/no) initial response to sP therapy. Human T1D onset differs from diabetes-prone mice by the frequent (~70%) occurrence of a transient remission phase ("honeymoon", see below) that begins sometime in the 1st year post onset and lasts from weeks to (sometimes) months (Module 1.2.3.3). In the present study, disease remission (euglycemia off insulin) might be difficult to distinguish from spontaneous honeymoon, except that it is expected to manifest in close proximity post-injection. While this phase-1 study cannot be aimed to generate significant efficacy data, the control cohort(s) make it possible to elucidate trends in a definitive fashion, in particular if patient treatment responses are also binary and if sP-induced remission has anywhere near the longevity of the murine therapy (equivalent to 6-8 human years), more common relapse and re-injection after even 1 year may clinically still represent a desirable effect, in particular if non-invasive drug delivery strategies, now in development, can be moved to application.

The next stage of the study, Stage C, is randomization. 20 eligible patients are recruited for randomization to intervention and 20 as the control cohort in the initial intervention period, terminated in each intervention patient 3 weeks later with an MMTT. Thus analysis in the first intervention group has both, pre-treatment and untreated control data.

About 1 week after the last intervention patient was injected, the control cohort crosses over to intervention status, undergo the pre-intervention MMTT, to receive the intervention about a week later: this 2nd intervention period terminates with a day 20 post-injection MMTT. Analysis of this group relies on pre-treatment data as controls. The rationale: T1D reversal is an essentially binary (yes/no) initial response to sP therapy.

Approximately 70% of patients with newly diagnosed Type 1 diabetes mellitus (T1D) temporarily restore to varying extent endogenous beta cell function following the initiation of insulin therapy (Bowden et al., 2008[3]). This period has been defined clinically in several ways, but most commonly it is now called "honeymoon" period, characterized by a daily insulin dose of <0.5 units per kg body weight per day (U/kg/d) and HbA1c≤7.0% (Bowden et al., 2008[3]). During honeymoon, blood glucose levels are frequently normal and stable—usually for weeks, sometimes for months—with little or no need for exogenous insulin and with near normal HbA1c, despite fluctuations in diet and exercise. But by 6 months past onset, nearly all and by 12 months all but very rare patients will have reverted to pre-honeymoon insulin needs and the full typical clinical T1D course and signs (Abdul-Rasoul et al., 2006[1]).

The mechanisms governing this transiently improved beta-cell function remain poorly understood. There is some consensus, that hyperglycemia around disease onset represents added beta-cell stress that functionally silences many beta cells still surviving and that insulin therapy should relieve that stress to considerable extent, sufficient for beta-cells to recover (or possibly even regenerate/re-differentiate) (van Belle et al., 2011[24]). Considerable normalization of elevated insulin resistance around disease onset would also contribute to improved metabolic control in honeymoon (Schober et al., 1984[25]), but it remains unclear how the declaredly auto-aggressive immune system can temporarily "shut down" its progressiveness: unfortunately there are few relevant data sets and there is no animal model for honeymoon. Nevertheless, the fact that honeymoon is common has generated consensus, that it may represent the most promising target of intervention therapies. Some 85% of new onset cases have no T1D family history and onset is the first time diabetes declares itself: pre-diabetes has no obvious symptoms for many years.

Unfortunately, as aptly implied by the term, honeymoon has great variability in extent and duration, lasting anywhere from weeks to months. Researchers have observed one exceedingly rare case of honeymoon-like relapsing-remitting T1D that lasted well over three decades before T1D was stable, with two of three offspring from this patient developing full T1D early and without honeymoon (Dosch et al. unpublished). Although extremely rare, such cases illustrate that physiological mechanisms exist, able to curb autoimmune progression, making successful intervention strategies an ultimately attainable goal.

Because the honeymoon remission phase is a period of stable metabolic control, it is important and promising to identify factors that control the duration of clinical remission in T1D. Several factors, including age, gender, pubertal status, metabolic abnormalities at the time of onset, HLA genotype, presence of diabetes-associated autoantibodies, have all been recognized to affect the likelihood of partial or complete remission in newly diabetic children (Biiyiikgebiz et al., 2001[21]). From the discussion of published studies it becomes clear that there are differences in age groupings and definitions that hinder firm conclusions at this time.

The honeymoon phase often commences within days or weeks of the start of insulin therapy, usually lasting for weeks, rarely for months. In order to determine frequency and duration of the honeymoon period after initiation of insulin therapy in newly diagnosed patients, a group of 103 diabetic children, younger than 12 years of age, was prospectively monitored. Partial remission occurred in 69%, complete remission occurred in three. The length of time until remission was 28.6±12 days, the honeymoon duration was 7.2±4.8 months (Abdul-Rasoul et al., 2006[1]).

A retrospective study involved 62 patients, diagnosed with T1D under the age of 18 years during the years 1991-1998 (Bowden et al., 2008[3]). Thirty-five patients (56.5%) entered partial remission. The length of time until remission was 1.36±1.03 months and positively correlated with insulin requirements at discharge from hospital.

To determine whether there are different rates of partial remission in preschool, school-age children and adolescents with T1D, 152 consecutive patients with newly diagnosed T1D were studied in 2004 (Bowden et al., 2008[3]). Patients were classified in three age-groups (group-1 (<5 years), group-2 (5-12 years) and group-3 (>12 years). Clinical characteristics at diagnosis, hemoglobin A1C (HbA1C) and total daily insulin dose (TDD) were analyzed in each age-class every three month over 1 year. Partial remission was defined as TDD≤0.5 units/kg/d, with HbA1C<8%. Young children (group-1, 26.8%) and adolescents (group-3, 29%) had low rates of partial remission compared with school-age children (group-2, 56%, p=0.002). At 12 months, group differences had disappeared: 13% (5/38) of group-1, 20% (11/56) of group-2 and 18% (8/44) of group-3 remained in partial remission.

The honeymoon period is different for each individual with T1D, the variables that govern each course remain ill-defined and different smaller studies can have considerably different outcomes. Data sets were obtained from 6.123 pediatric 111) patients (<18 years old), who were treated in 157 pediatric centers and were observed for 36 months at the same center starting from diagnosis (Dost et at, 2007[22]). Analyses from this large multicenter study of diabetic children included roles for age, gender and pubertal status at onset of disease in shaping the amount of insulin required and the clinical disease remission, which in this study occurred during the first three years of the disease.

Multiple statistical analyses were performed to identify factors influencing honeymoon duration. Results revealed that partial remission (insulin<0.5 U/kg/d and HbA1c<7.0%) developed in 1992 children (32.5%), most within the first 3 months after diagnosis. Among those, 21% entering remission were younger than 5 years, 37% were 5-10 years old, 37% of patients were 10-15 years old and 5% were adolescents, 15-17 years old at disease onset. These analyses consolidate earlier report that the rates of partial remission are higher in younger patients.

|  | Age at onset | | | | |
| --- | --- | --- | --- | --- | --- |
|  | <5 years | 5-10 years | <10 years | 10-15 years | >15 years |
| Boys | 10.4 ± 10.2 | 8.76 ± 9.24 | 9.36 ± 9.36 | 8.76 ± 9.24 | 11.04 ± 10.8 |
| Girls | 8.4 ± 9.2 | 7.56 ± 8.16 | 7.8 ± 8.52 | 9.36 ± 9.72 | 11.04 ± 10.08 |
| P | 0.013 | 0.085 | 0.0039 | 0.31 | 0.98 |

Remission lasted for an average of 0.74±0.77 years (8.8 months) and was significantly shorter in children <10 years of age at T1D onset, compared to patients with later onset, as shown in the table above. The shorter honeymoon phase in younger children might be related to a higher rate of ketoacidosis and/or a more abnormal metabolic situation at diabetes onset. Children with pubertal diabetes onset had a longer remission phase, conceivably reflecting anti-inflammatory hormonal testosterone effects, since there were gender differences in honeymoon duration, with longer remission periods in boys (estrogen is more pro-inflammatory). However, this gender effect was mainly observed in children <10 years old (p=0.0039), where sex hormone levels are low and no significant gender difference was found in patients with diabetes onset during or after puberty. Thus the role of hormonal effects in onset and post-onset remission remains unclear.

The extent of metabolic imbalance at disease onset seems to be an essential factor that determines the prevalence and length of remission (Abdul-Rasoul et al., 2006[1]). The severity of metabolic abnormalities at the time of diagnosis, i.e. the relatively long duration of disease prior treatment, large blood glucose elevations, high HbA1C values, the duration of glucosuria and high insulin requirements to establish euglycemia (due to insulin resistance) is associated with shorter clinical remission in children with T1D (Vetter et al., 1982[23]).

Diabetic ketoacidosis (DKA) at diagnosis lowers the honeymoon prevalence, perhaps reflective of a decreased capacity for beta-cell recovery after the beginning of insulin therapy. DKA is a consequence of insulin deficiency, corresponding hyperglycemia with the burning of fatty acids accumulating systemic ketone bodies, thus generating potentially fatal metabolic acidosis. Children younger than 5 years or older than 12 years of age are more likely to develop DKA than children between 5 and 12 years of age, reasons are elusive (Bowden et al., 2008[3])

Endogenous insulin secretion is assessed by measurement of C-peptide. Coded by the insulin gene, the 31 amino acid C-peptide is cleaved from pro-insulin and both are co-secreted at a one-to-one molar ratio. Measurement of baseline and stimulated C-peptide (after glucagon or a mixed meal) in patients with recent-onset T1D is used as a measure of residual, global beta cell function or -mass. Several studies have shown that higher C-peptide levels are positively associated with honeymoon during the first six months of T1D and C-peptide levels are a good predictor of honeymoon during the first year of T1D (Zmyslowska et al. 2007[26]).

In a study of 268 patients with recently diagnosed T1D, patients were stratified by gender, age, and season at diabetes onset (Agner et al., 1987[27]). During the first 36 months of disease, an assessment was performed for basal C-peptide, HbA1c, and insulin dose per kilogram. Total disease remission was set as complete discontinuation of insulin therapy for at least 1 week with stable metabolic control, while partial remission was set as an insulin need of ≤50% of the insulin dose at discharge from the hospital. During the first 18 months of disease, 12.3% of the patients developed total remission for a median of 6 months, and 18.3% of patients developed partial remission, also for a median of 6 months. Patients entering honeymoon had significantly higher basal C-peptide levels than those who did not. From these, unfortunately not too consonant studies, a general conclusion can be drawn, that known factors predicting honeymoon and honeymoon duration include pre-pubertal onset, male gender, mild initial metabolic derangement and absence of frank ketoacidosis.

Overall, T1D honeymoon remains poorly understood, in particular with respect to autoimmune progression and its almost certain, but unproven, transient suppression. Nevertheless, available data and broad consensus identify the honeymoon period a natural and promising target of intervention therapies aimed at its therapeutic extension. Islet autoimmunity does not disappear during honeymoon, as judged by T1D-associated auto-antibodies, but clearly lacks progression since there is sufficient endogenous beta-cell derived insulin (and c-peptide) production. The honeymoon process therefore must reflect the acute emergence of regulatory lymphocytes which down-regulate autoimmune effector function—there are no data, even cues why and how that would occur. The consistent failures of toxic immunosuppression trials in recent-onset T1D patients emphasize that overall conclusion: immunosuppression kills regulatory lymphocyte pools as well as effector cells.

Collectively, the observation of honeymoon in a large proportion of recent-onset T1D patients implies that physiological mechanisms for breaking disease progression do exist and effective interventions during this hold promise if they support the physiological escape from disease progression obvious in honeymoon. Such interventions must either slow or arrest the progression of autoimmune beta-cell destruction/de-differentiation. The substance P pancreas injection trial is the first to employ a non-toxic physiological treatment strategy in T1D which is effective in animal models to achieve just that target profile. It relieves the chronic neuropeptide deficiency that characterizes the key genetic T1D susceptibility in TRPV1-mutant rodents and hypofunctional TRPV1 allele selection in T1D-susceptible humans. This strategy promises to precipitate and extend honeymoon by years and repeat injections are effective in the same animal models. The hallmark T1D trials, DCCT/EDIC, determined that even a limited (months) period of (near) normal glucose metabolism has major impact on the devastating T1D complications 2-4 decades later: while substance P therapy is not a cure of the genetic underpinnings of T1D, it promises major, positive, long-term impact on the harsh realities of living with T1D and its enormous multi-billion annual costs long-term of complications.

In one embodiment, the amount of the sP administered to an individual is the range of 50-100 nmol/kg.

EXAMPLES

Example 1

Study Cohorts—Sample Size N=52

52 eligible, consented children or adolescents aged 10-18 years are recruited with informed, parental consent and patient assent, as appropriate. These patients have been diagnosed with T1D within ≤30 months and have a basal c-Peptide level at recruitment of ≥0.2 pmoles/mL.

Patients with recent onset T1D (CDA guidelines <http://www.diabetes.ca/for-professionals/resources/2008-cpg/>, see below), with positive measures of typical metabolic dysfunction, insulin replacement need; T1D- associated B- & T cell autoimmunity is added, as this T1D element is one of the direct therapy targets. The patients were diagnosed at or referred to the Hospital For Sick Children, Toronto, ON, e.g. by one of the associated SickKids Satellite Diabetes Centers in the greater Toronto area. Patients are eligible for the trial, provided that: 1. they are between 10- 18 years old; 2. patients are <30 months from diagnosis and have no other chronic illnesses other than treated hypothyroidism—not uncommon in T1D; 3. parents/caregivers and, when agreeable to them, patients have received verbal explanations of the trial and have viewed the Health Canada approved, educational video describing sP therapy in diabetes. Explanations include familiarization with the potential risks associated with a visceral angiogram, the injection of sP, anesthesia and the (in humans) untested possibility of intervention failure, prior to providing their informed consent, in writing, for the study and the procedural angiogram.

sP treatment may not benefit patients that have normal sP secretory activity, controlled by the TRPV1 genotype. To stratify the cohort in this small initial study for the most likely responders, and to reduce possible risks for unlikely responders, patients are eligible for intervention if they carry at least one of the polymorphic, T1D-associated TRPV1 alleles that are prevalent in T1D patients/families. Since the large TRPV1 sequencing program in Europe and North America may remain incomplete for years to come, it is possible that sequences may be encountered that are as yet unclassified. Therefore, a bioassay has been developed that measures occupancy status of lymphocyte NK1R (the main sP receptor which internalizes rapidly following sP-ligation). Most T1D patients have abnormally elevated levels of unoccupied surface NK1R, reflective of low steady state sP levels, and this assay can be used to confirm intervention eligibility. These data are described and discussed in the HC Investigator Brochure.

Based on sequence and functional data, it is expected that as many as 20% of possible recruits may fail this last, dual inclusion set which is designed to focus the study on the theoretically most likely sP-responsive population. Larger follow-up studies may have the power to distinguish patient subpopulations and emphasize or de-emphasize these inclusion criteria. The rationale: T1D reversal is an essentially binary (yes/no) initial response to sP therapy. Human T1D onset differs from diabetes-prone mice by the frequent (~70%) occurrence of a transient remission phase ("honeymoon") that begins sometime in the 1st year post onset and lasts from weeks to months (Module 1.2.3.3). In the present study, disease remission (euglycemia off insulin) is expected to be induced that is difficult to distinguish from spontaneous honeymoon, except that it is expected to manifest rapidly within hours-days post injection, rather than over a period of days. While this phase-1 study cannot be aimed to generate significant efficacy data, the control cohort(s) makes it possible to elucidate trends in a definitive fashion, in particular if patient treatment responses are also binary and if sP-induced remission has anywhere near the longevity of the murine therapy (equivalent to ~6 human years, more common relapse and re-injection after even 1 year may clinically still represent a desirable effect, in particular if the non-invasive drug delivery strategies in development can be developed.

A number of permanent, acquired or congenital as well as transient conditions preclude participation in this study: 1. In patients with the common, transient remission ("honeymoon", <0.5 U insulin/kg), there is no acute measure of drug effects and sP intervention treatment may be delayed until disease relapses, using rising insulin needs to ≥1 U/kg as relapse measure. 2. Patients have known co-morbidities, including ACE-inhibitor treated hypertension as well as chromosomal abnormalities, impacting one or more organ systems. Common childhood infectious diseases with fever ≥38° C. would lead to re-scheduling. 3. Pregnancy. 4. Patients with a known radiographic contrast allergy. 5. Overweight (BMI 85-95th percentile) or obese (BMI>95th percentile for age) patients with a BMI>90th percentile for age are not be eligible for this initial study, as c-Peptide levels are modified by elevated weight. 6. Parents plan to leave Toronto imminently and follow-up cannot be assured.

Since the preclinical and animal data (Razavi et al., 2006[9]) indicate that the treatment is most likely to benefit patients that have a reduced function of TRPV1 channel. Therefore, the potential candidate must be a carrier of at least one T1D-associated allele in the TRPV1 gene: rs8065080 c.1753A>C/T/G (p.Ile585Leu/p.Ile585Phe/p.Ile585Val) or; rs224534 c.1406C>T (p.Thr469Ile) or; rs222749 c.271C>T (p.Pro91Ser) or; rs222747 c.945G>C (p.Met315Ile). Sequence listings of PCR primers for amplification and sequencing of specific TRPV1 missense variants are provided (SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8). All PCR products, 500-688 bp long, are amplified from genomic DNA extracted from buccal swab samples. Purified PCR products are re-sequenced, by the certified Genomics Quebec facility, from both ends and the consensus genotype is determined. Patient genotypes are communicated only to the lead physician who, with his advisors, confirms the eligibility for the trial based on patient's genotype.

Figure 7:
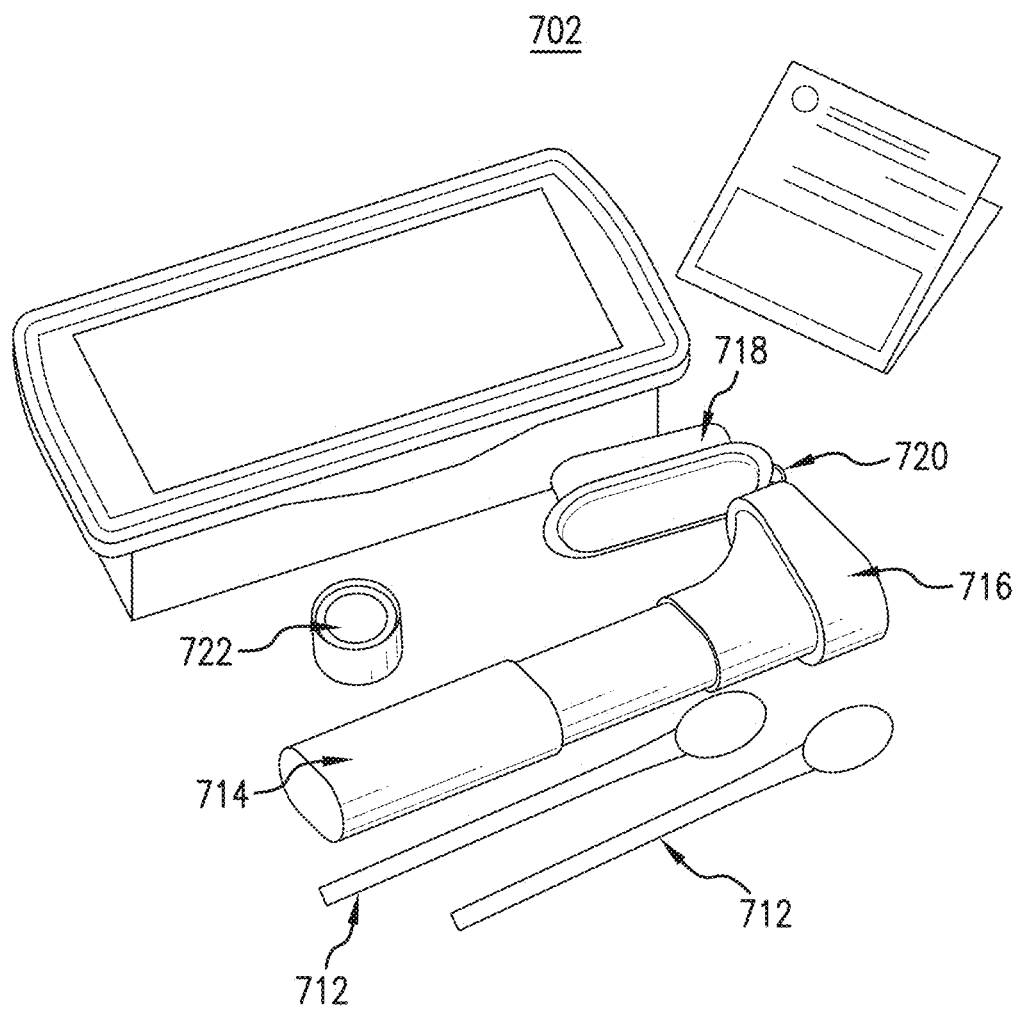
FIG. 7 shows a DNA collection kit that may be used in one embodiment of the present invention.

Prior to treatment all consented patients provide a buccal swab sample for DNA analyses using a DNA collection kit. The DNA is used to amplify and sequence specific exons of the TRPV1 gene to identify a patient's genotypes, which will be used to determine the eligibility for the study. Patients with wild type TRPV1 genotypes are not eligible for this trial, as they are unlikely to benefit from the treatment and their T1D disease might have developed due to alternative pathogenic mechanisms. FIG. 7 shows a DNA collection kit 702 that may be used in one embodiment of the present invention to collect DNA samples. DNA collection kit 702 includes swabs 712, a tube 714, a funnel 716 that screws onto tube 714, a funnel lid 718 that is connected to funnel 716 by a flexible strap 720, and a small cap 722 for tube 714. Although a particular DNA collection kit is shown in FIG. 7, other types of DNA collection kits may be used in various embodiments of the present invention to collect DNA samples.

Example 2

Drug Formulation

Liquid, for Injection, substance P in 0.9% Sodium Chloride, for Injection USP. SP-R/A™: 2mg sP/mL and SP-PED™: 0.5mg sP/mL, vials: 1mL each. cGMP-grade active pharmaceutical ingredient, API (Polypeptide Inc, San Diego, CA, 98% pure), cGMP sterile drug manufacture outsourced to Dalton PharmaServices, Toronto. Production procedures and validation are complete and follow industry standards; manufacturing data.

Example 3

Dosage Regimen

Dose finding and toxicity study—Stage A, 12 patients randomized to receiving 10-50-100 or 250 nmoles/kg i.a., 3 patients per dose group. The treatment dose was originally calculated from a count of cell surface-expressed sP receptors, NK1R, per mg mouse pancreas tissue, obtained from serial sections and extrapolated to the whole organ—not a procedure that can be duplicated in T1D patients. The sP dose was calculated to give a 100-fold saturation per surface receptor extrapolating to 2 nmol/20g mouse, adjusting for in-tissue dwelling time and drug half life. This dose was indeed effective. New onset mouse T1D has a massive lymphocytic infiltration and many of the pancreatic surface NK1R receptors are actually carried by these infiltrating cells, in fact, most of these cells are legitimate and almost certainly prerequisite targets of sP therapy, as it triggers rapid lymphocyte death in recently activated lymphocytes (Module 1.2.3.6). This dramatically reduces autoimmune effector cells in the pancreas and its associated lymph node tissue. The new onset pancreas inflammatory lesion of human T1D may be less dense, but data available are insufficient for exact comparisons, generating such data is not presently feasible. The standard sP dose in mouse experiments was 2 nmol/mouse (i.e. 100 nm sP/kg BW) where a dose of 0.2 nmol/mouse had only partial effects. On this background, it is estimated that a dose of 100 nmol/kg BW may provide a similar degree of acute NK1R ligation in situ as was achieved in sP therapy-responsive new onset T1D mice.

Example 4

Washout Period

Based on agreements during the pre-CTA meeting (May, 2012) no placebo is used, and ultimately, all patients receive an sP injection. However, if warranted by significant diabetes reversal rates, patients in the Stage A dose finding group, who did receive an ineffectively low sP dose, may be offered a second injection towards the end of the intervention period. With a vascular half-life time of as low as <30 seconds, up to a minute in some locales, the washout period for sP would be extremely short.)

Example 5

Pre-Study Screening and Baseline Evaluation

Standard patients care, SOP at the Hospital, includes initial as well as repeated measurements of a number of metabolic variables, but in addition, by 1-5 weeks prior sP intervention, at least one measurement is required of T1D-relevant B and T cell autoreactivities, as well as one MMTT. Added tests, such as the sequencing of TRPV1 allelic sequence diversity and of NK1R (sP receptor) occupancy rates was described and discussed in exclusion criteria, above.

Example 6

Treatment/Assessment Visits

A detailed description of the intervention and post-intervention process is provided. As described, it may be overly cautious and represent a patient stress that may well outweigh that of the intervention itself: the routine femoral injection procedure is usually done on an outpatient base. By the end of the Stage A toxicity and dose finding period, it is determined if the observation period and intensive supervision can be safely reduced with DSMB agreement.

Study-relevant baseline data are important. As a rule, new onset data are available in the patient charts. The study requires the following blood tests, drawn 1-5 weeks before recruitment and randomization: HbA1c, T1D-associated B- and T-cell autoreactivity, pancreas and liver function tests and, critically, an MMTT, generating data on c-Peptide (basal, peak, AUC), fasting and stimulated insulin & glucose levels). The study aims to begin Stage A (dosing, toxicity) when 12 patients are or about to signing informed consent. Recruitment for Stage B (Intervention) continues from there.

Duplication of sampling with standard care sampling is avoided through routinely close coordination by the trial physician and the trial Monitor. Research Pharmacy is notified of patient scheduling, including Name, HSC ID, body weight (kg) 1-3 weeks before scheduled intervention.

The regular (adolescent) sP formulation, SP-R/A™ (BLUE label), contains 2 mg sP/mL in saline, the pediatric formulation, SP-PED™ (YELLOW label), 0.5 mg sP/mL. Both formulations are stored frozen at below −20° C.

The research pharmacy receives from the study staff, patient ID, body weight and scheduling to re-calculate and confirm or correct the intervention dose and the appropriate number of blue or yellow vials, communicating by email with the trial physician by day minus-2. An Excel®-based automated calculator has been developed and validated by VanilloidGenetics Inc and was provided to the study team. A written prescription order, stating patient Name, ID, BW and the final dose as well as the volumes from blue-coded sP-R/A and/or yellow-coded sP-Ped to be combined in a 10 mL sterile syringe. On the morning of intervention, the required drug vials are removed from its secure cold storage, signed out of storage, placed in a sealed, sterile plastic bag, thawed at room temperature and stored on water-ice until signed over to trial staff, in this case the lead physician and the trial monitor. The ready-to-use vials are transported to the intervention OR and delivered to the IGT team performing the injection.

On the morning of study entry (day-1), consented T1D patients have a scheduled fasting blood glucose measurement. In the rare case where a recent MMTT dataset is not available, such a patient undergoes an MMTT. After the MMTT, a modified insulin dose may be prescribed if required and patients are released to go home, after seeing an anesthesia and IGT consult to discuss the next day intervention, unless these meetings have already been concluded previously.

The next morning, fasted intervention patients are admitted to hospital between 8-9 am. Provided that it has been confirmed that the intervention drug is on-hand from the Pharmacy. Patients are prepared for and receive brief, standard anesthesia for delivery of sP via the celiac artery. The IGT imaging team has routinely carried out femoral angiograms in their clinical practice as well as performing sP celiac injections for the entire canine study without adverse events. Stage A patients are randomized to one of 4 groups, 3 patients each, to receive 10, 50, 100 or 250 nmoles sP/kg. The given dose is injected and patients enter a monitoring phase, initially leaving 2d between groups, as permitted by OR availability and scheduling constraints. The data generated in Stage A, in particular improved fasting glucose levels and reduction in insulin need are used to identify possible sP dose responses. All daily glucometer readings are uploaded frequently to the study site. The 3-4 initial (Stage A) patients are admitted overnight and then stay near the Hospital for at least the first 2 days, as decided on clinical grounds by the PI. The conclusion of Stage-A is expected to identify the single Stage B intervention dose, a process that involves staff, and the study board. The rationale: Stage A generates the first patient data. T1D reversal in recent onset diabetic mice occurs within hours along mechanistic pathways quite well understood. It is expected that sP effects might be rather prompt in patients as well, given the fast kinetics of sP-receptor ligation with its positive survival effects in beta cells and its negative survival effects on the pancreatic autoimmune-infiltrate. The Stage-A strategy covers a judicious drug dose range and it proceeds cautiously although there is no reason to expect any drug toxicities—and it generates the experience needed and the drug dose used for Stage B. The stage A strategy and cohort size was discussed, approved and incorporated in the final minutes of the pre-CTA meeting with Health Canada (Investigators Brochure, Module 1.2.3.1). In this pre-CTA meeting, it was also discussed that if an effective sP dose emerges in Stage A, it would be ethical to offer Stage A patients that received a lower dose, a second injection at the optimal dose by the end of Stage B, about 4 weeks after study start and as scheduling allows. This does not jeopardize conclusions derived from this study stage or the study overall, as repeat injections after treatment failure are ultimately part of the follow-up plan, albeit at intervals anticipated in the range of years.

After completion of Stage A, these patients enter Stage C (follow up), unless it is decided to offer those patients that received a suboptimal dose a second injection with the Stage B dose. Such patients might be added to an intervention cohort in Stage B. During completion of injections in Stage A, recruitment for Stage B continues: pre-set randomization is done in groups of 5 patients each for the intervention and control cohorts. Stage B interventions begin when the first group of 10 (5 controls, 5 intervention) has been consented, and it continues until 40 gave consent—unless unexpected adverse events trigger a study moratorium or DSMB-sanctioned protocol changes. The DSMB has been constituted with three senior, academically well respected T1D physicians from the U.S and one from Europe: the DSMB will communicate frequently with the study team and as a board via Skype. All observations made in the Stage B toxicity and dose-finding study, as well as any intervention-ascribed adverse events are communicated promptly to the DSMB, advisory board (email, phone) and adverse, in particular sP-associated events to the REB: there now is an on-line reporting path for adverse events to Health Canada. The DSMB has the power and obligation to stop or modify the trial in face of unexpected adverse events. In the absence of intervention-ascribed adverse events, 40 recruited and eligible patients then receive the study dose in a modified cross-over study design: 20 intervention patients are controlled by 20 at that point un-injected, control patients, which in turn cross over to become intervention patients, controlled by their own pre-intervention data, 3 weeks old.

The injection protocol is described as: following catheter placement into the celiac artery, the dose finding sP amounts or the Stage B study intervention dose (10, 50, 100 or 250 nmol/kg BW, dissolved in 5 or 10 mL saline (see above), are injected over a 3 minute period. The rationale: Steady rate injection was used in all mouse studies, alternative rate injection timing were compared in the canine study without finding any differences.

After introduction of patients and parents to the study, and if interested in participating in the intervention and/or control group, the parents and child are seen in the Hospital IGT Clinic, in advance of the procedure, when a celiac angiogram is explained in detail. The risks are outlined. These include local groin issues (bleeding & hematoma, pseudoaneurysm, arterial dissection, arterial thrombosis/stenosis, AV-fistula, pain); local issues in the celiac territory (thrombosis, spasm, arterial dissection, bleeding); systemic issues (contrast allergy, X-ray exposure, air embolism, stroke); injection related (pancreatitis, liver dysfunction, cholecystitis); innovative drug status (off label). An informed consent is signed by the parents and if appropriate, the patient assents.

Blood work is organized for the day prior to the procedure including CBC, coagulation (INR, PTT) as well as typing and screening for 0 units, these tests are in addition to those listed above, but typing and screening can be done several weeks prior intervention. The date of last menstrual period is checked for girls >12 years and pregnancy tested in accordance with current Hospital policy. A baseline diagnostic abdominal ultrasound is arranged to specifically examine the pancreas, liver, gall bladder and spleen. An anesthesia consult is organized prior to the intervention.

Example 7

Concomitant Medication

Brief anesthesia during celiac angiogram and sP injection, standard recovery, local pain management injection site, insulin prescription based on frequent blood glucose measurements.

Example 8

Efficacy Variables and Analysis

The main measurements are MMTT-derived, diabetes-associated variables prior to and after the 3 weeks post-intervention period, the core variable for analysis being c-Peptide (basal, peak and AUC). Secondary analysis includes insulin need, and estimates of insulin resistance, fasting and stimulated blood glucose—unless modified by clinical requirements, all values are derived from MMTTs prior to, at the end of the intervention and at 6- and possibly 12 months thereafter.

Example 9

Safety Variables and Analysis

Routine blood chemistries include two measurements of pancreas, liver and intestinal markers during Stage A of the study. If no abnormal values are observed, this number is reduced to one measurement 4-7d after intervention.

The study follows Health Canada ICH E2A reporting Standards. Possible adverse events are monitored and recorded by trial staff & Monitor. Two qualified physicians, NOT part of the study team, form a stand-by AE team, one always on home-based call, their call schedule posted to trial staff. Minor AEs are communicated for discussion and analysis within 24 hr, at most 3 hr for Serious/severe AE. All AEs are described, entered into study and patient records, identified as study-related/unrelated, drug treatment-related/unrelated using the SickKids adverse event form (Study Protocol, pp.: 22). Serious/severe AEs are communicated to the REB, HC and DSMB in writing.

Example 10

Statistical Analysis

This study implements recommendations of a recent NIH-TrialNet T1D meta study, regarding clinical assay strategies, statistical approaches and interpretations (Greenbaum et al., Diabetes: 2012[5]; Lachin et al., PLoS One: 2011[8]). For Stage A (toxicity & dose finding), the first 12 patients recruited are randomized (SAS procedure), each to one of the four sP doses (10-50-100-250 nmoles/kg). All patients undergo a pre-intervention MMTT prior intervention, the low dose first, highest last, constituting the toxicity study. If during this dose escalation process, there are drug-associated, unexpected adverse events, the DSMB is consulted immediately to determine if further dose escalation should continue. Stage A will be completed with an MMTT 3 weeks after the last Stage A patient is injected, and before the start of Stage B (intervention), although recruitment, consents and pre-intervention MMTT will be obtained earlier. Stage B (efficacy trends, n=40): In this two-sequence, two-period, single treatment, modified crossover study, 40 patients are randomized (SAS procedure) into the initial treatment or control groups (n=20 each). Patients in the treatment group undergo a baseline MMTT 7-30 days prior intervention.

These patients then receive the single-injection study intervention with the sP dose selected in Stage A; 3 weeks later, each treated patient undergoes an MMTT. This ends Stage B for the given patient and provide all his/her data for the primary study objective. These data are classifying that patient as responder or non-responder based on c-Peptide values and lessened insulin need, comparing the final MMTT to pre-intervention data as well as relevant data sets from the control group. The treated patient then crosses over to Stage C (follow up), with Home glucose measurements and insulin doses are electronically uploaded regularly through a secure study website and the data included in the analysis. The frequency of glucose measurements may be determined by the PI, as will be that of weekly-monthly phone contact between the study team and the family (e.g. weekly, monthly).

The (so far untreated) control group undergoes an initial MMTT during the second half of the initial intervention period I. After completion of this period I, control patients cross over from control to treatment status and be scheduled to receive the study intervention (period II), which, for each patient, ends 3 weeks after injection of the last patient, and completed with an MMTT: pre- and post-intervention Data are compared as above, the patients then crossing over to Stage C (follow up). Since each patient receives only a single injection, the typical concerns about "wash-out" periods between the 2 periods do not apply. In addition, the intervention (sP) has an extremely short tissue half-life (<1 minute). Formal data analysis is performed using the GEE (generalized estimation equation) approach to build a population-averaged marginal model. This model accounts for correlation within the same patient and the time-varying covariate (treatment effect). The primary measure is c-Peptide, basal or stimulated, both measured in MMTTs and/or major reduction or absence of insulin need. Secondary measures include insulin levels, glycemia. Different correlation structures are investigated, and the most appropriate correlation matrices are selected.

The final model estimates the treatment, period, sequence effects, as well as relationships between treatment response, age, age-at-onset, intervention time past onset, gender. The analysis determines if any single or combined marker predicts sP responsiveness/unresponsiveness. Hb1AC and autoimmune markers are compared by repeated measures ANOVA pre-intervention and at 3 and 6 (and, if extended, 12) months of the study, as the systemic changes measured are slower to emerge than immediate metabolic effects. If there is consensus among the clinical team, advisory Board and DSMB, the follow up period may be extended, using a monitoring algorithm based on the study experience generated. The study should terminate with an MMTT for final data analysis. SAS 9.3 and PROC GEMOD with repeated statement are used throughout the analysis.

The statistical power of this small initial translation study enables analysis in several ways. The scientific and clinical need to monitor several key disease markers enhances the power in combinatorial comparisons with Bonferroni corrections where appropriate. At the 6-month study endpoint, with at best very few, if any controls in honeymoon, three sP Responders would generate a significant result. If sP therapy in fact generates a form of honeymoon, where full remission is defined as <0.5 U insulin/kg/d, approximately the same power would apply proportionately. From previous experiences in the field (Herold et al., N. Engl. J. Med.: 2002[6]), the analysis of secondary outcomes, in particular HbA1c, c-Peptide (AUC, peak, fasting) may be most sensitive and the several consecutive measurements in each patient adds considerable power and confidence in the statistical analysis despite its small size (Greenbaum et al., Diabetes: 2012[5]; Lachin et al., PLoS One: 2011[8]).

The brevity (3 wk) of the dosing and intervention stages, as well as the non-intrusive character of the follow-up (Stage C, uploading of glucometer and insulin data, 2 Hospital visits, initially bi-weekly phone calls) is not likely to promote loss-to-follow-up, (LTF). However, LTFs might be anticipated with some preference in non-responders. If this scenario begins to appear possible, despite extra efforts of the study team, and to enhance the statistical power of the study, standard care Hospital chart data from up to 30 T1D patients not related to the study but followed by standard care at the Hospital since diagnosis over the past 30 months are collected. Anonymized data sets on insulin use, age at onset, fasting glucose and, where available, some oral glucose tolerance test, are tabulated by a small team of students, not otherwise related to the study.

REFERENCES

The following references are referred to above and/or describe technology that may be used with the present invention and contents and disclosures of the following references are incorporated herein by reference:

1. Abdul-Rasoul, M., Habib, H., and Al-Khouly, M. "The honeymoon phase' in children with type 1 diabetes mellitus: frequency, duration, and influential factors." *Pediatr. Diabetes* 7, 101-107 (2006).
2. Akirav, E., Kushner, J. A., and Herold, K. C. "Beta-cell mass and type 1 diabetes: going, going, gone?" *Diabetes* 57, 2883-2888 (2008).
3. Bowden, S. A., Duck, M. M., and Hoffman, R. P. "Young children (<5 yr) and adolescents (>12 yr) with type 1 diabetes mellitus have low rate of partial remission: diabetic ketoacidosis is an important risk factor." *Pediatr. Diabetes* 9, 197-201 (2008).
4. Dorfman, R., Tsui, H., Salter, M. W., and Dosch, H.-M. "TRPV1 Genetics." In Vanilloid Receptor TRPV1 in Drug Discovery: Targeting Pain and Other Pathological Disorders, Faltynek, ed. (Hoboken, N. J., USA: John Wiley & Sons, Inc.), pp. 176-229 (2010).
5. Greenbaum, C. J., Beam, C. A., Boulware, D., Gitelman, S. E., Gottlieb, P. A., Herold, K. C., Lachin, J. M., McGee, P., Palmer, J. P., Pescovitz, M. D., et al. "Fall in C—peptide during first 2 years from diagnosis: evidence of at least two distinct phases from composite Type 1 Diabetes TrialNet data." *Diabetes* 61, 2066-2073 (2012).
6. Herold, K. C., Hagopian, W., Auger, J. A., Poumian-Ruiz, E., Taylor, L., Donaldson, D., Gitelman, S. E., Harlan, D. M., Xu, D., Zivin, R. A., et al. "Anti-CD3 monoclonal antibody in new-onset type 1 diabetes mellitus." *N. Engl. J. Med.* 346, 1692-1698 (2002).
7. Koh, Y. H., Tamizhselvi, R., Moochhala, S., Bian, J. S., and Bhatia, M. (2011). "Role of protein kinase C in caerulein induced expression of substance P and neurokinin-1-receptors in murine pancreatic acinar cells." *J. Cell. Mol. Med.* 15, 2139-2149 (2011).
8. Lachin, J. M., McGee, P. L., Greenbaum, C. J., Palmer, J., Pescovitz, M. D., Gottlieb, P., and Skyler, J. "Sample size requirements for studies of treatment effects on beta-cell function in newly diagnosed type 1 diabetes." *PLoS One* 6, e26471 (2011).
9. Razavi, R., Chan, Y., Afifiyan, F. N., Liu, X. J., Wan, X., Yantha, J., Tsui, H., Tang, L., Tsai, S., Santamaria, P., et al. TRPV1+ sensory neurons control beta cell stress and islet inflammation in autoimmune diabetes. *Cell* 127, 1123-1135 (2006).
10. Talchai, C., Xuan, S., Kitamura, T., DePinho, R. A., and Accili, D. (2012). Generation of functional insulin-producing cells in the gut by Foxo1 ablation. *Nat. Genet.* 44, 406-412, S401 (2012).
11. Talchai, C., Xuan, S., Lin, H. V., Sussel, L., and Accili, D. Pancreatic beta Cell Dedifferentiation as a Mechanism of Diabetic beta Cell Failure. *Cell* 150, 1223-1234 (2012).
12. Tsui, H., Chan, Y., Tang, L., Winer, S., Cheung, R. K., Paltser, G., Selvanantham, T., Elford, A. R., Ellis, J. R., Becker, D. J., et al. Targeting of pancreatic glia in type 1 diabetes. *Diabetes* 57, 918-928 (2008).
13. Tsui, H., Dorfman, R., Salter, M. W., and Dosch, H.-M. The Role of TRPV1 in Diabetes. In Vanilloid Receptor TRPV1 in Drug Discovery: Targeting Pain and Other Pathological Disorders, Faltynek, ed. (Hoboken, N. J., USA: John Wiley & Sons, Inc.), pp. 384-469 (2010).

14. Tsui, H., Paltser, G., Chan, Y., Dorfman, R., and Dosch, H. M. 'Sensing' the link between type 1 and type 2 diabetes. *Diabetes Metab. Res. Rev.* 27, 913-918 (2011).
15. Tsui, H., Razavi, R., Chan, Y., Yantha, J., and Dosch, H. M. 'Sensing' autoimmunity in type 1 diabetes. *Trends Mol. Med.* 13, 405-413 (2007).
16. Tsui, H., Winer, S., Chan, Y., Truong, D., Tang, L., Yantha, J., Paltser, G., and Dosch, H. M Islet glia, neurons, and beta cells. *Ann. N. Y. Acad. Sci.* 1150, 32-42 (2008).
17. Tsui, H., Winer, S., Jakowsky, G., and Dosch, H. M Neuronal elements in the pathogenesis of type 1 diabetes. *Rev. Endocr. Metab. Disord.* 4, 301-310 (2003).
18. Winer, D. A., Winer, S., Shen, L., Wadia, P. P., Yantha, J., Paltser, G., Tsui, H., Wu, P., Davidson, M. G., Alonso, M. N., et al. B cells promote insulin resistance through modulation of T cells and production of pathogenic IgG antibodies. *Nat. Med.* 17, 610-617 (2011).
19. Winer, S., Chan, Y., Paltser, G., Truong, D., Tsui, H., Bahrami, J., Dorfman, R., Wang, Y., Zielenski, J., Mastronardi, F., et al. Normalization of obesity-associated insulin resistance through immunotherapy. *Nat. Med.* 15, 921-929 (2009).
20. Winer, S., Tsui, H., Lau, A., Song, A., Li, X., Cheung, R. K., Sampson, A., Afifiyan, F., Elford, A., Jackowski, G., et al. Autoimmune islet destruction in spontaneous type 1 diabetes is not beta-cell exclusive. *Nat. Med.* 9, 198-205 (2003).
21. Biiyiikgebiz A, Cemeroglu A P, Bober E, Mohn A, Chiarelli F. Factors influencing remission phase in children with type 1 diabetes mellitus. *J. Pediatr. Endocrinol. Metab.* 14(9):1585-96 (2001).
22. Dost A, Herbst A, Kintzel K, Haberland H, Roth C L, Gortner L, Holl R W. Shorter remission period in young versus older children with diabetes mellitus type 1. *Exp. Clin. Endocrinol. Diabetes* 115(1):33-7 (2007).
23. Vetter U, Heinze E, Kohne E, Teller W M, Kleihauer E. Relation between the degree of initial metabolic decompensation and the duration of the remission phase in type I diabetes mellitus. *Eur. J. Pediatr.* 138(1):63-6 (1982).
24. van Belle T L, Coppieters K T, von Herrath M G. Type 1 diabetes: etiology, immunology, and therapeutic strategies. *Physiol. Rev.* 91(1):79-118 (2011).
25. Schober E, Schernthaner G, Frisch H, Fink M. Beta-cell function recovery is not the only factor responsible for remission in type I diabetics: evaluation of C-peptide secretion in diabetic children after first metabolic recompensation and at partial remission phase. *J. Endocrinol. Invest.;* 7(5):507-12 (1984).
26. Zmyslowska A, Mlynarski W, Szadkowska A, Bodalski J. [Prediction of clinical remission using the C-peptide level in type 1 diabetes in children]. *Pediatric Endocrinol. Diabetes Metab.* 13(2):71-4 (2007).
27. Agner T, Damm P, Binder C. Remission in IDDM: prospective study of basal C-peptide and insulin dose in 268 consecutive patients. *Diabetes Care.* 10(2):164-9 (1987).
28. Bober E, Diindar B, Búyükgebiz A. Partial remission phase and metabolic control in type 1 diabetes mellitus in children and adolescents. *J. Pediatr. Endocrinolo-Metab.* 14(4):435-41 (2001).
29. Haneda, E., Higuchi, M., Maeda, J., Inaji, M., Okauchi, T., Ando, K., Obayashi, S., Nagai, Y., Narazaki, M., Ikehira, H., et al. In vivo mapping of substance P receptors in brains of laboratory animals by high-resolution imaging systems. *Synapse* 61, 205-215 (2007).
30. Michelgard, A., Appel, L., Pissiota, A., Frans, O., Langstrom, B., Bergstrom, M., and Fredrikson, M. Symptom provocation in specific phobia affects the substance P neurokinin-1 receptor system. *Biol. Psychiatry* 61, 1002-1006 (2007).
31. Chan, Y. C., and Leung, P. S. Co-operative effects of angiotensin II and caerulein in NFkappaB activation in pancreatic acinar cells in vitro. *Regul. Pept.* 166, 128-134 (2011).
32. Dib, M., Zsengeller, Z., Mitsialis, A., Lu, B., Craig, S., Gerard, C., and Gerard, N. P. A paradoxical protective role for the proinflammatory peptide substance P (NK1R) in acute hyperoxic lung injury. *Am. J. Physiol. Lung Cell. Mol. Physiol.* 297, L687-697 (2009).
33. Mansfield, C. S., Watson, P. D., and Jones, B. R. Specificity and sensitivity of serum canine pancreatic elastase-1 concentration in the diagnosis of pancreatitis. *J. Vet. Diagn. Invest.* 23, 691-697 (2011).
34. Trivedi, S., Marks, S. L., Kass, P. H., Luff, J. A., Keller, S. M., Johnson, E. G., and Murphy, B. Sensitivity and specificity of canine pancreas-specific lipase (cPL) and other markers for pancreatitis in 70 dogs with and without histopathologic evidence of pancreatitis. *J. Vet. Intern. Med.* 25, 1241-1247 (2011).
35. Wan, H., Yuan, Y., Qian, A., Sun, Y., and Qiao, M. Pioglitazone, a PPARgamma ligand, suppresses NFkappaB activation through inhibition of IkappaB kinase activation in cerulein-treated AR42J cells. *Biomed. Pharmacother.* 62, 466-472 (2008).
36. Hasel, C., Bhanot, U. K., Heydrich, R., Strater, J. & Moller, P. Parenchymal regression in chronic pancreatitis spares islets reprogrammed for the expression of NFkappaB and IAPs. *Lab. Invest.* 85, 1263-1275 (2005).

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method comprising the following step:
(a) detecting whether a mutation in transient receptor potential vanilloid-1 (TRPV1) gene that generates a hypofunctional phenotype of TRPV1 is present in a genomic DNA of an individual with resent onset type 1 diabetes (T1D); and
(b) delivering a therapeutically effective amount of a pharmaceutical composition comprising substance P (sP) into celiac artery of the individual when the presence of a hypofunctional TRPV1 allele is detected in the genomic DNA of the individual; wherein the therapeutically effective amount of the pharmaceutical composition comprises at least 10 nmol/kg of substance P.

2. The method of claim 1, wherein the genomic DNA of the individual is obtained from a saliva sample from the individual.

3. The method of claim 1, wherein the therapeutically effective amount of the pharmaceutical composition completely reverses recent onset T1D.

4. The method of claim 1, wherein the therapeutically effective amount of the pharmaceutical composition transiently reverses recent onset T1D for months to years.

5. The method of claim 1, wherein the pharmaceutical composition aids storage, production and release of insulin by beta cells in a pancreas.

6. The method of claim 1, wherein the pharmaceutical composition is delivered into the celiac artery of the individual over a period of at least three minutes.

7. The method of claim 1, wherein the therapeutically effective amount of the pharmaceutical composition comprises the substance P dissolved in about 5 or 10 mL of saline.

8. The method of claim 1, wherein the individual is a human diagnosed with type 1 diabetes no longer than 30 months and has a basal c-Peptide level of no less than 0.2 pmol/mL.

9. The method of claim 1, wherein the therapeutically effective amount of the pharmaceutical composition comprises about 50 nmol/kg to about 100 nmol/kg of the substance P.

10. The method of claim 1, wherein the therapeutically effective amount of the pharmaceutical composition comprises about 100 nmol/kg to about 250 nmol/kg of the substance P.

11. The method of claim 1, wherein the therapeutically effective amount of the pharmaceutical composition comprises at least 250 nmol/kg of the substance P.

12. The method of claim 1, wherein the presence of a mutation in TRPV1 gene is detected by sequencing polymerase chain reaction (PCR) products amplified from the genomic DNA of the individual with PCR primers of specific TRPV1 missense variants; wherein the PCR primers comprise sequences selected from the group consisting of SEQ ID NO:1, SEQ ID NO:2, SEQ ID NO:3, SEQ ID NO:4, SEQ ID NO:5, SEQ ID NO:6, SEQ ID NO:7, and SEQ ID NO:8.

13. The method of claim 1, wherein the mutation in TRPV1 gene comprises 1753A>C/T/G.

14. The method of claim 1, wherein the mutation in TRPV1 gene comprises 1406C>T.

15. The method of claim 1, wherein the mutation in TRPV1 gene comprises 271C>T.

16. The method of claim 1, wherein the mutation in TRPV1 gene comprises 945G>C.

* * * * *

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Designed PCR primer for amplification and sequencing of specific TRPV1 missense variants.

```
<400> SEQUENCE: 1
agaattgctt gaacccagga ggca                                              24

<210> SEQ ID NO 2
<211> LENGTH: 24
<212> TYPE: DNA
<213> ORGANISM: Artificial Sequence
<220> FEATURE:
<223> OTHER INFORMATION: Designed PCR primer for amplification and
      sequencing of specific TRPV1 missense variants.

<400> SEQUENCE: 2
agctgagaac cagcaaagca aacc                                              24

<210> SEQ ID NO 3
<211> LENGTH: 24
<212> TYPE: DNA
<213> ORGANISM: Artificial Sequence
<220> FEATURE:
<223> OTHER INFORMATION: Designed PCR primer for amplification and
      sequencing of specific TRPV1 missense variants.

<400> SEQUENCE: 3
tactttcaag cttgcctgcc ttgg                                              24

<210> SEQ ID NO 4
<211> LENGTH: 24
<212> TYPE: DNA
<213> ORGANISM: Artificial Sequence
<220> FEATURE:
<223> OTHER INFORMATION: Designed PCR primer for amplification and
      sequencing of specific TRPV1 missense variants.

<400> SEQUENCE: 4
attgtaagat gctccgcttg gcac                                              24

<210> SEQ ID NO 5
<211> LENGTH: 24
<212> TYPE: DNA
<213> ORGANISM: Artificial Sequence
<220> FEATURE:
<223> OTHER INFORMATION: Designed PCR primer for amplification and
      sequencing of specific TRPV1 missense variants.

<400> SEQUENCE: 5
gcaaggatga agaaatggag cagc                                              24

<210> SEQ ID NO 6
<211> LENGTH: 24
<212> TYPE: DNA
<213> ORGANISM: Artificial Sequence
<220> FEATURE:
<223> OTHER INFORMATION: Designed PCR primer for amplification and
      sequencing of specific TRPV1 missense variants.

<400> SEQUENCE: 6
aagtccaagt gtctgtggct ggta                                              24

<210> SEQ ID NO 7
<211> LENGTH: 24
<212> TYPE: DNA
<213> ORGANISM: Artificial Sequence
<220> FEATURE:
<223> OTHER INFORMATION: Designed PCR primer for amplification and
      sequencing of specific TRPV1 missense variants.

<400> SEQUENCE: 7
```

-continued tttgggcaga gacagaggga gttt                    24

<210> SEQ ID NO 8
<211> LENGTH: 24
<212> TYPE: DNA
<213> ORGANISM: Artificial Sequence
<220> FEATURE:
<223> OTHER INFORMATION: Designed PCR primer for amplification and
      sequencing of specific TRPV1 missense variants.

<400> SEQUENCE: 8
ttcttctgtt ccaccctagg cagt                    24